United States Patent
Bolotin et al.

(10) Patent No.: US 8,257,682 B2
(45) Date of Patent: *Sep. 4, 2012

(54) COMPOSITIONS FOR DELIVERY OF THERAPEUTICS AND OTHER MATERIALS

(75) Inventors: Elijah M. Bolotin, Bothell, WA (US); Gerardo M. Castillo, Bothell, WA (US)

(73) Assignee: PharmaIn Corporation, Seattle, WA (US)

( * ) Notice: Subject to any disclaimer, the term of this patent is extended or adjusted under 35 U.S.C. 154(b) by 389 days.

This patent is subject to a terminal disclaimer.

(21) Appl. No.: 12/551,203

(22) Filed: Aug. 31, 2009

(65) Prior Publication Data

US 2010/0098636 A1    Apr. 22, 2010

Related U.S. Application Data

(60) Division of application No. 11/766,623, filed on Jun. 21, 2007, now Pat. No. 7,635,463, and a continuation-in-part of application No. 11/428,803, filed on Jul. 5, 2006, now Pat. No. 7,790,140, which is a continuation of application No. 10/378,100, filed on Feb. 27, 2003, now Pat. No. 7,138,105, application No. 12/551,203, which is a continuation-in-part of application No. 11/266,002, filed on Nov. 3, 2005, now Pat. No. 7,589,169, which is a continuation of application No. 11/112,879, filed on Apr. 22, 2005, now abandoned.

(60) Provisional application No. 60/360,350, filed on Feb. 27, 2002, provisional application No. 60/564,710, filed on Apr. 23, 2004, provisional application No. 60/805,574, filed on Jun. 22, 2006.

(51) Int. Cl.
*A61K 51/00* (2006.01)
*A61M 36/14* (2006.01)

(52) U.S. Cl. ............ 424/1.65; 424/1.11; 424/1.49; 424/1.69; 424/1.73

(58) Field of Classification Search .............. 424/1.11, 424/1.49, 1.65, 1.73, 9.1, 9.3, 9.4, 9.5, 9.6, 424/9.7, 9.8; 534/7, 10–16; 530/300

See application file for complete search history.

(56) References Cited

U.S. PATENT DOCUMENTS

| | | | |
|---|---|---|---|
| 4,857,311 A | 8/1989 | Domb et al. | |
| 5,118,666 A | 6/1992 | Habener | |
| 5,120,712 A | 6/1992 | Habener | |
| 5,527,524 A | 6/1996 | Tomalia et al. | |
| 5,554,388 A | 9/1996 | Illum | |
| 5,593,658 A | 1/1997 | Bogdanov et al. | |
| 5,605,672 A | 2/1997 | Bogdanov et al. | |
| 5,614,492 A | 3/1997 | Habener | |
| 5,631,018 A | 5/1997 | Zalipsky et al. | |
| 5,661,025 A | 8/1997 | Szoka, Jr. et al. | |
| 5,663,387 A | 9/1997 | Singh | |
| 5,681,544 A | 10/1997 | Schmitt-Willich et al. | |
| 5,714,166 A | 2/1998 | Tomalia et al. | |
| 5,744,166 A | 4/1998 | Illum | |
| 5,763,585 A | 6/1998 | Nag | |
| 5,776,894 A | 7/1998 | Albert et al. | |
| 5,837,747 A | 11/1998 | Soon-Shiong et al. | |
| 5,871,710 A | 2/1999 | Bogdanov et al. | |
| 5,891,418 A | 4/1999 | Sharma | |
| 5,929,031 A | 7/1999 | Kerwin et al. | |
| 5,958,909 A | 9/1999 | Habener | |
| 5,977,084 A | 11/1999 | Szoka, Jr. et al. | |
| 6,006,753 A | 12/1999 | Efendic | |
| 6,051,549 A | 4/2000 | Roberts et al. | |
| 6,113,946 A | 9/2000 | Szoka, Jr. et al. | |
| 6,124,273 A | 9/2000 | Drohan et al. | |
| 6,159,443 A | 12/2000 | Hallahan | |
| 6,162,462 A | 12/2000 | Bolotin et al. | |
| 6,225,284 B1 | 5/2001 | Albert et al. | |
| 6,274,175 B1 | 8/2001 | Gombotz et al. | |
| 6,284,727 B1 | 9/2001 | Kim et al. | |
| 6,338,859 B1 | 1/2002 | Leroux et al. | |
| 6,348,069 B1 | 2/2002 | Vacanti et al. | |
| 6,365,173 B1 | 4/2002 | Domb et al. | |
| 6,395,299 B1 | 5/2002 | Babich et al. | |
| 6,443,898 B1 | 9/2002 | Unger et al. | |
| 6,447,753 B2 | 9/2002 | Edwards et al. | |
| 6,458,373 B1 | 10/2002 | Lambert et al. | |
| 6,468,532 B1 | 10/2002 | Hsei et al. | |
| 6,475,779 B2 | 11/2002 | Mathiowitz et al. | |
| 6,492,560 B2 | 12/2002 | Wilbur et al. | |
| 6,509,323 B1 | 1/2003 | Davis et al. | |

(Continued)

FOREIGN PATENT DOCUMENTS

JP    10158195    6/1998

(Continued)

OTHER PUBLICATIONS

U.S. Appl. No. 60/360,350, filed Feb. 27, 2002, Bolotin.

(Continued)

*Primary Examiner* — D L Jones

(74) *Attorney, Agent, or Firm* — Wilson Sonsini Goodrich & Rosati

(57) ABSTRACT

This disclosure relates to compositions for delivering agents to a subject, and in particular, to compositions for delivery of therapeutic agents or diagnostic agents in the presence or absence of targeting moieties. In part, this disclosure relates to compositions comprising a hydrophobic group with a first end and a second end, a first metal binding domain linked to the hydrophobic group, a metal ion capable of being chelated to the first metal binding domain, and an agent linked to a second metal binding domain capable of chelating to the metal ion.

19 Claims, 28 Drawing Sheets

U.S. PATENT DOCUMENTS

| | | | |
|---|---|---|---|
| 6,521,211 | B1 | 2/2003 | Unger et al. |
| 6,521,736 | B2 | 2/2003 | Watterson et al. |
| 6,579,851 | B2 | 6/2003 | Goeke et al. |
| 6,583,111 | B1 | 6/2003 | DiMarchi et al. |
| 6,586,524 | B2 | 7/2003 | Sagara et al. |
| 6,589,549 | B2 | 7/2003 | Shih et al. |
| 6,627,228 | B1 | 9/2003 | Milstein et al. |
| 6,703,037 | B1 | 3/2004 | Hubbell et al. |
| 6,703,359 | B1 | 3/2004 | Young et al. |
| 6,706,689 | B2 | 3/2004 | Coolidge et al. |
| 6,747,006 | B2 | 6/2004 | Efendic |
| 6,828,303 | B2 | 12/2004 | Kim et al. |
| 6,849,708 | B1 | 2/2005 | Habener |
| 6,884,628 | B2 | 4/2005 | Hubbell et al. |
| 6,894,024 | B2 | 5/2005 | Coolidge et al. |
| 6,899,883 | B2 | 5/2005 | Dupre |
| 6,982,248 | B2 | 1/2006 | Coolidge et al. |
| 6,998,137 | B2 | 2/2006 | Shih et al. |
| 7,049,284 | B2 | 5/2006 | Drucker |
| 7,101,843 | B2 | 9/2006 | Glaesner et al. |
| 7,138,105 | B2 * | 11/2006 | Bolotin .................. 424/9.36 |
| 7,138,486 | B2 | 11/2006 | Habener |
| 7,144,863 | B2 | 12/2006 | DeFelippis et al. |
| 7,199,217 | B2 | 4/2007 | DiMarchi et al. |
| 7,259,233 | B2 | 8/2007 | Dodd et al. |
| 7,285,529 | B2 | 10/2007 | Summerton |
| 7,329,644 | B2 | 2/2008 | Saviano et al. |
| 7,534,449 | B2 | 5/2009 | Saltzman et al. |
| 7,589,169 | B2 * | 9/2009 | Bolotin .................. 530/308 |
| 7,635,463 | B2 * | 12/2009 | Bolotin et al. ........... 424/1.65 |
| 7,790,140 | B2 * | 9/2010 | Bolotin .................. 424/1.65 |
| 2002/0015737 | A1 | 2/2002 | Shih et al. |
| 2002/0132254 | A1 | 9/2002 | Twu |
| 2003/0050237 | A1 | 3/2003 | Kim et al. |
| 2003/0119734 | A1 | 6/2003 | Flink et al. |
| 2003/0220251 | A1 | 11/2003 | Knudsen et al. |
| 2003/0224974 | A1 | 12/2003 | Bolotin |
| 2003/0229034 | A1 | 12/2003 | Waugh et al. |
| 2004/0092432 | A1 | 5/2004 | During et al. |
| 2004/0162241 | A1 | 8/2004 | Efendic |
| 2004/0197369 | A1 | 10/2004 | Hubbell et al. |
| 2004/0209803 | A1 | 10/2004 | Baron et al. |
| 2004/0220105 | A1 | 11/2004 | Jensen et al. |
| 2004/0235726 | A1 | 11/2004 | Jakubowski et al. |
| 2004/0266683 | A1 | 12/2004 | Hathaway et al. |
| 2005/0008661 | A1 | 1/2005 | Fereira et al. |
| 2005/0014681 | A1 | 1/2005 | Minamitake et al. |
| 2005/0143303 | A1 | 6/2005 | Quay et al. |
| 2005/0148497 | A1 | 7/2005 | Khan et al. |
| 2005/0159356 | A1 | 7/2005 | Dong et al. |
| 2005/0215475 | A1 | 9/2005 | Ong et al. |
| 2005/0239705 | A1 | 10/2005 | Dake et al. |
| 2005/0260259 | A1 | 11/2005 | Bolotin |
| 2006/0003935 | A1 | 1/2006 | Pan et al. |
| 2006/0019874 | A1 | 1/2006 | Radhakrishnan et al. |
| 2006/0030838 | A1 | 2/2006 | Gonnelli |
| 2006/0057137 | A1 | 3/2006 | Steiness |
| 2006/0074025 | A1 | 4/2006 | Quay et al. |
| 2006/0093660 | A1 | 5/2006 | Bolotin |
| 2006/0128627 | A1 | 6/2006 | Goke et al. |
| 2006/0172001 | A1 | 8/2006 | Ong et al. |
| 2006/0178304 | A1 | 8/2006 | Juul-Mortensen et al. |
| 2006/0183682 | A1 | 8/2006 | Juul-Mortensen |
| 2006/0199763 | A1 | 9/2006 | Knudsen et al. |
| 2006/0239924 | A1 | 10/2006 | Bolotin |
| 2006/0247167 | A1 | 11/2006 | Schlein et al. |
| 2006/0286129 | A1 | 12/2006 | Sarubbi |
| 2007/0041951 | A1 | 2/2007 | Egan et al. |
| 2007/0141006 | A1 | 6/2007 | Livoreil et al. |
| 2007/0141145 | A1 | 6/2007 | Castillo et al. |
| 2007/0244296 | A1 | 10/2007 | Tomalia et al. |
| 2007/0298006 | A1 | 12/2007 | Tomalia et al. |
| 2008/0015263 | A1 | 1/2008 | Bolotin et al. |
| 2009/0053169 | A1 | 2/2009 | Castillo et al. |
| 2010/0069293 | A1 | 3/2010 | Bolotin et al. |
| 2010/0158806 | A1 | 6/2010 | Bolotin et al. |
| 2010/0221184 | A1 | 9/2010 | Bolotin et al. |

FOREIGN PATENT DOCUMENTS

| | | |
|---|---|---|
| WO | WO 94/05203 A1 | 3/1994 |
| WO | WO 97/33552 A1 | 9/1997 |
| WO | WO 98/42383 A1 | 10/1998 |
| WO | WO 01/28569 A1 | 4/2001 |
| WO | WO 01/39815 A2 | 6/2001 |
| WO | WO 01/87925 A2 | 11/2001 |
| WO | WO 01/39815 A3 | 1/2002 |
| WO | WO 01/87925 A3 | 8/2002 |
| WO | WO 03/072143 A1 | 9/2003 |
| WO | WO 2004/022004 A2 | 3/2004 |
| WO | WO 2004/022004 A3 | 12/2004 |
| WO | WO 2005/084180 A2 | 9/2005 |
| WO | WO 2005/084180 A3 | 12/2005 |
| WO | WO 2007/024899 A2 | 3/2007 |
| WO | WO 2007/030706 A1 | 3/2007 |
| WO | WO 2007/048190 A1 | 5/2007 |
| WO | WO 2007/056681 A2 | 5/2007 |
| WO | WO 2007/082331 A1 | 7/2007 |
| WO | WO 2007/024899 A3 | 11/2007 |
| WO | WO 2007/056681 A3 | 4/2008 |

OTHER PUBLICATIONS

U.S. Appl. No. 60/464,601, filed Apr. 22, 2003, Bolotin.

U.S. Appl. No. 60/532,337, filed Dec. 26, 2003, Quay et al.

Ahrén, et al. Improved glucose tolerance and insulin secretion by inhibition of dipeptidyl peptidase IV in mice. Eur. J. Pharmacol. 2000; 404(1-2):239-45.

Barton. Protective Group in Organic Chemistry. Chapter 2. MeOmie, ed. Plenum Press. New York, 1973.

Bogdanov, et al. A new macromolecule as a contrast agent for MR angiography: preparation, properties, and animal studies. Radiology. 1993; 187(3):701-6.

Bogdanov, et al. Long-circulating blood pool imaging agents. Adv Drug Del Revs. 1995; 16:335-348.

Bonner-Weir, et al. Imaging the Pancreatic Beta Cell. 1999; http://www.niddk.nih.gov/fund/reports/beta_imaging_report_2.htm.

Brand, et al. Pharmacological treatment of chronic diabetes by stimulating pancreatic beta-cell regeneration with systemic co-administration of EGF and gastrin. Pharmacol Toxicol. 2002; 91(6):414-20.

Bulotta, et al. Cultured pancreatic ductal cells undergo cell cycle re-distribution and beta-cell-like differentiation in response to glucagon-like peptide-1. J. Mol. Endocrinol. 2002; 29(3):347-60.

Buteau, et al. Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells. Diabetologia. 1999; 42(7):856-64.

Caliceti, et al. Pharmacokinetic and biodistribution properties of poly(ethylene glycol)-protein conjugates. Advanced Drug Delivery Reviews. 2003; 55: 1261-77.

Callahan, et al. Preclinical evaluation and phase I clinical trial of a 99mTc-labeled synthetic polymer used in blood pool imaging. AJR Am J Roentgenol. 1998; 171(1):137-43.

Clark, D. Guide for Care of Use of Laboratory Animals. National Research Council. 1996; pp. i-xii and 1-128.

Cunninghanm, et al. Dimerization of human growth hormone by zinc. Science. Aug. 2, 1991;253(5019):545-8.

Druncker, D. Enhancing incretin action for the treatment of type 2 diabetes. Diabetes Care. 2003; 26(10):2929-40.

Ettaro, et al. Cost-of-illness studies in diabetes mellitus. Pharmacoeconomics. 2004; 22(3):149-64.

Farilla, et al. Glucagon-like peptide 1 inhibits cell apoptosis and improves glucose responsiveness of freshly isolated human islets. Endocrinology. 2003; 144(12):5149-58.

Gappa, et al. The effect of zinc-crystallized glucagon-like peptide-1 on insulin secretion of macroencapsulated pancreatic islets. Tissue Eng. 2001; 7(1):35-44.

Gupta, et al. Inflammation: imaging with methoxy poly(ethylene glycol)-poly-L-lysine-DTPA, a long-circulating graft copolymer. Radiology. 1995; 197(3):665-9.

Hrkach, et al. Poly(L-lactic acid-co-amino acid) graft copolymers: A class of functional biodegradable biomaterials. Hydrogel and Biodegradable Polymers for Bioapplications, ACS Symposium Series No. 627. Ottenbrite, et al., eds. American Chemical Society, 1996: 93-101 (chapter 8).

Hrkach, et al. Synthesis of poly(L-lactic acid-co-L-lysine) graft copolymers. Macromolecules. 1995; 28: 4736-9.

Hui, et al. Glucagon-like peptide 1 induces differentiation of islet duodenal homeobox-1-positive pancreatic ductal cells into insulin-secreting cells. Diabetes. 2001; 50(4):785-96.

Lapidot, et al. Use of esters of N-hydroxysuccinimide in the synthesis of N-acylamino acids. J Lipid Res. 1967; 8(2): 142-5.

Leonard, et al. Trimethylene Bridges as Synthetic Spacers for the Detection of Intramolecular Interaction. Accounts of Chem. Res. 1979; 12:423.

List of the abbreviation utilized by Organic Chemists of Ordinary Scill in the art. Journal of Organic Chemistry. First issue of each volume. 2005; pp. 26A-27A.

March. Quantitative Treatments of the Effect of Structure on Reactivity. Advanced Organic Chemistry. New York, NY: McGraw Hill Book Company, 1977, 251-9.

MicroGD™. Accessed at http://pharmain.com/MacroGdPage.html. Accessed Feb. 29, 2008.

Nielsen, et al. Pharmacology of exenatide (synthetic exendin-4) for the treatment of type 2 diabetes. Curr. Opinion Investig. Drugs. 2003; 4(4):401-5.

Otto, et al. Recognition and separation of isoenzymes by metal chelates: Immobilized metal ion affinity partitioning of lactate dehydrogenase isoenzymes. Journal of Chromatography. 1993; 644: 25-33.

Perry, et al. The glucagon-like peptides: a double-edged therapeutic sword? Trends in Pharmacol. Sci. 2003; 24(7):377-83.

Prosser, et al. Novel chelate-induced magnetic alignment of biological membranes. Biophysical Journal. 1998; 75: 2163-9.

Röstin, et al. B-Domain deleted recombinant coagulation factor VIII modified with monomethoxy polyethylene glycol. Bioconjug Chem. 2000; 11(3): 387-396.

Scrocchi, et al. Identification of glucagon-like peptide 1 (GLP-1) actions essential for glucose homeostasis in mice with disruption of GLP-1 receptor signaling. Diabetes. 1998; 47(4):632-9.

Shapiro, et al. Clinical islet transplant: current and future directions towards tolerance. Immunol. Rev. 2003; 196:219-36.

Suginoshita, et al. Liver targeting of interferon-β with a liver-affinity polysaccharide based on metal coordination in mice. Journal of Pharmacology and Experimental Therapeutics. 2001; 298(2): 805-11.

Tabata, et al. Growth factor release from amylopectin hydrogel based on copper coordination. J Control Release. Dec. 4, 1998;56(1-3):135-48.

Tabata, et al. Targeting of tumor necrosis factor to tumor by use of dextran and metal coordination. J Control Release. May 20, 1999;59(2):187-96.

Terpe, K. Overview of tag protein fusions: from molecular and biochemical fundamentals to commercial systems. Appl Microbiol Biotechnol, 2003; 60: 523-33.

Tourrel, et al. Glucagon-like peptide-1 and exendin-4 stimulate beta-cell neogenesis in streptozotocin-treated newborn rats resulting in persistently improved glucose homeostasis at adult age. Diabetes. 2001; 50(7):1562.

Urusova, et al. GLP-1 inhibition of pancreatic islet cell apoptosis. Trends Endocrinol Metab. 2004; 15(1):27-33.

Van Broekhoven, et al. A novel system for convenient detection of low-affinity receptor-ligand interactions: Chelator-lipid liposomes engrafted with recombinant CD4 bind to cells expressing MHC class II. Immunology and Cell Biology. 2001; 79(3): 274-84.

Weast, R. Periodic table of elements, CAS version. Handbook of Chemistry and Physics, 67th Edition. Boca Raton, FL: CRC Press, 1986-1987. (Inside cover).

Wiedeman, et al. Dipeptidyl peptidase IV inhibitors for the treatment of impaired glucose tolerance and type 2 diabetes. Curr. Opinion Investig. Drugs. 2003; 4(4):412-420.

Xu, et al. Exendin-4 stimulates both beta-cell replication and neogenesis, resulting in increased beta-cell mass and improved glucose tolerance in diabetic rats. Diabetes. 1999; 48(12):2270-6.

European search report dated Nov. 29, 2005 for Application No. 03716207.

Greene, et al. Protection for the amino group. In Protective Groups in Organic Synthesis, 2nd Edition. New York, NY: Wiley & Sons, 1991, chapter 7. 1991; 309-405.

International search report dated May 26, 2006 for PCT Application No. US05/14128.

International search report dated Jul. 7, 2008 for PCT Application No. US07/88010.

International search report dated Jul. 24, 2003 for PCT Application No. US03/05937.

Porath, et al. Metal chelate affinity chromatography, a new approach to protein fractionation. Nature. Dec. 18, 1975;258(5536):598-9.

International search report and written opinion dated Dec. 15, 2010 for PCT Application No. US2010/000809.

* cited by examiner

LEGENDS
  Hydrophobic group

) First metal binding domain

Metal

LEGENDS

— Hydrophobic group

⊂ First Metal binding Domain

● Metal

⊃● Load molecule with second metal binding domain

| LEGENDS | |
|---|---|
| ▰▰▰ | Hydrophobic group |
| ⟩ | First metal binding domain |
| ● | Metal |
| ⊂ | Second metal binding domain |
| ●⊂ | Load molecule with second metal binding domain |
| ▪▴▪▴▪ | Hydrophilic group |

1.

2.

3.

1.

2.

3.

1.

2.

3.

1.

2.

3.

COMPOSITIONS FOR DELIVERY OF THERAPEUTICS AND OTHER MATERIALS

CROSS-REFERENCE

This application is a divisional of U.S. patent application Ser. No. 11/766,623 filed Jun. 21, 2007 now U.S. Pat. No. 7,635,463 which is a continuation-in-part of U.S. patent application Ser. No. 11/428,803 filed Jul. 5, 2006 now U.S. Pat. No. 7,790,140 which is a continuation of U.S. patent application Ser. No. 10/378,100 filed Feb. 27, 2003, now U.S. Pat. No. 7,138,105 issued on Nov. 21, 2006, which claims the benefit of priority under 35 U.S.C. 119(e) to U.S. Provisional Application No. 60/360,350 filed Feb. 27, 2002. This application is also a continuation-in-part of U.S. patent application Ser. No. 11/266,002 filed Nov. 3, 2005 now U.S. Pat. No. 7,589,169 which is a continuation of U.S. patent application Ser. No. 11/112,879, filed Apr. 22, 2005, now abandoned which claims the benefit of priority to U.S. Provisional Patent Application Ser. No. 60/564,710, filed Apr. 23, 2004. This application also claims the benefit of priority under 35 U.S.C. 119(e) to U.S. Provisional Application No. 60/805,574, filed Jun. 22, 2006. These applications are incorporated herein by reference.

TECHNICAL FIELD

This disclosure relates to compositions for delivering agents to a subject, and in particular, to compositions for delivery of therapeutic agents, diagnostic agents, and other materials in the presence or absence of targeting groups.

BACKGROUND OF THE INVENTION

The development of new drugs, formulations and other systems for administration of physiologically active peptides, proteins, organic drugs, other therapeutics and materials is driven by the need to achieve the desirable physiological effects. With respect to peptides and proteins, many of them have been observed to be unstable in the gastro-intestinal tract and therefore may need to be stabilized or protected or delivered via systemic circulation. In addition, peptides and proteins that have low molecular masses tend to have short biological half-lives due to their efficient removal from systemic circulation via kidneys. For example, a fraction of these peptides and proteins can also be removed via reticuloendothelial uptake due to recognition by monocyte/macrophages or as a result of opsonization by complement components. Many peptides and proteins can also lose their activity in vivo due to proteolysis (peptide bond cleavage).

In part to circumvent these undesirable effects, a drug delivery system may be used. There are several drug delivery strategies that can be useful for peptide and protein delivery in vivo. First, a continuous systemic infusion of drug via a pump can be employed. This strategy has proven efficient in clinical practice but may be impractical for outpatients requiring high levels of mobility. This strategy also has associated disadvantages including quality of life and potential intravenous (I.V.) line infections.

Second, peptides and proteins can be included in an implantable pump comprised of a capsule with a membrane allowing diffusion of the drug, for example, at a desirable release rate. Due to limited volume of these capsules, peptides and proteins are often used in a concentrated formulation which leads to a loss of solubility due to aggregation and potential loss of specific activity. In most cases, the drug is usually released into the extracellular space and distributed in lymphatics. Overall concentration of peptide or protein may be affected by local lymph node activity and the efficacy of lymph node drainage of the implantation site. There is also a potential of host reaction to capsule material but in general, this side effect is infrequent.

Third, the drug release system can be made biodegradable as a result of encapsulation or inclusion into degradable drug delivery vehicles or carriers, e.g. polymeric matrices, particles or membrane vesicles (liposomes). These delivery systems are usually either implantable or injectable. Implantable drug delivery systems are often placed under the epidermis where the components of the system are usually slowly degraded as a result of biological activity of surrounding cells (i.e. as a result of the release of enzymes degrading chemical bonds that hold these implants together).

SUMMARY OF THE INVENTION

In one embodiment, a composition may include a carrier, a metal ion and an agent. The carrier may include a hydrophobic group having a first end and a second end, and a first metal binding domain linked to the first end of the hydrophobic group. The agent may be linked to a second metal binding domain. The first metal binding domain and the second metal binding domain may be capable of chelating the metal ion.

In another embodiment, a composition may include a carrier, a metal ion and an agent. The carrier may include a hydrophilic group having a first end and second end, a first metal binding domain (FMBD) linked to the first end of the hydrophilic group, and a hydrophobic group linked to the second end of the hydrophilic group. The agent may be linked to a second metal binding domain. The first metal binding domain and the second metal binding domain may be capable of chelating the metal ion.

INCORPORATION BY REFERENCE

All publications, patents and patent applications mentioned in this specification are herein incorporated by reference to the same extent as if each individual publication or patent, or patent application was specifically and individually indicated to be incorporated by reference.

BRIEF DESCRIPTION OF THE DRAWINGS

All publications and patent applications mentioned in this specification are herein incorporated by reference to the same extent as if each individual publication or patent application was specifically and individually indicated to be incorporated by reference.

DETAILED DESCRIPTION OF THE INVENTION

In part, the present invention is directed to a composition with a metal bridge that connects an agent of interest to a carrier. For example, a composition may include a carrier, a metal ion and an agent. The carrier and the agent may each be linked to a metal binding domain. In turn, the metal binding domains may chelate the metal ion. The carrier, metal binding domains, metal ion and agent may form supermolecular structures including microemulsions, liposomes, and micellar and reverse micellar structures.

In one embodiment of the present invention, the carrier is a hydrophobic group linked to a first metal binding domain (FMBD). The FMBD may chelate a metal ion, which is further chelated by a second metal binding domain (SMBD) linked to an agent of interest (see FIGS. 1 and 2). This composition can be represented by [L-SMBD-Me-FMBD-H]; where H=hydrophobic group: Me=metal ion: FMBD=first metal binding domain; SMBD=second metal binding domain: L=agent or load molecule. The meaning of hydrophobic group, MBDs, metal ion, hydrophilic group, targeting group and agent will become apparent in the subsequent disclosure below. After administration of the composition to a subject, the agent may be released in a sustained manner. The compositions of the present invention may self-organize into supermolecular structures.

Figure 1:
FIG. 1 depicts a non-limiting diagram of one of the components of the present invention comprising a carrier. The carrier comprises a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside).
Figure 1:
Figure 1:
Figure 1:
Figure 1:
Figure 1:
Figure 2:
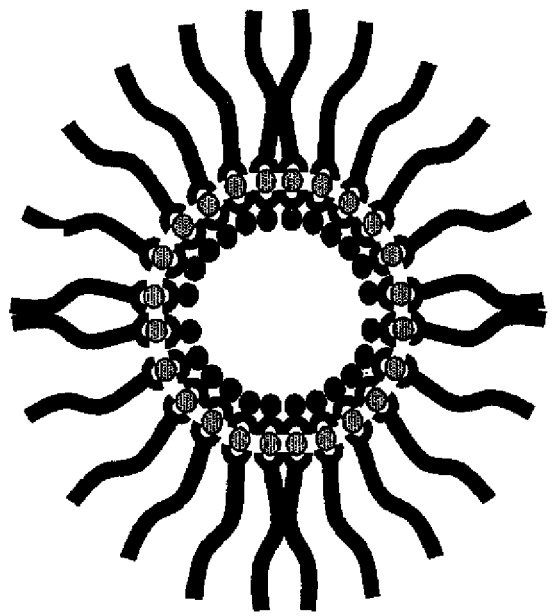
FIG. 2 depicts a non-limiting diagram of a supermolecular structure of one of the embodiments of the present invention. The supermolecular structure comprises a carrier. The carrier comprises a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). In the figure is a two-dimensional diagram depicting the formation of a supermolecular structure which is only one of many possible supermolecular structures that may form depending on the solvent or excipient. The structure presented can form, for example, in water in oil environments where water is inside the structure and oil outside.
Figure 3:
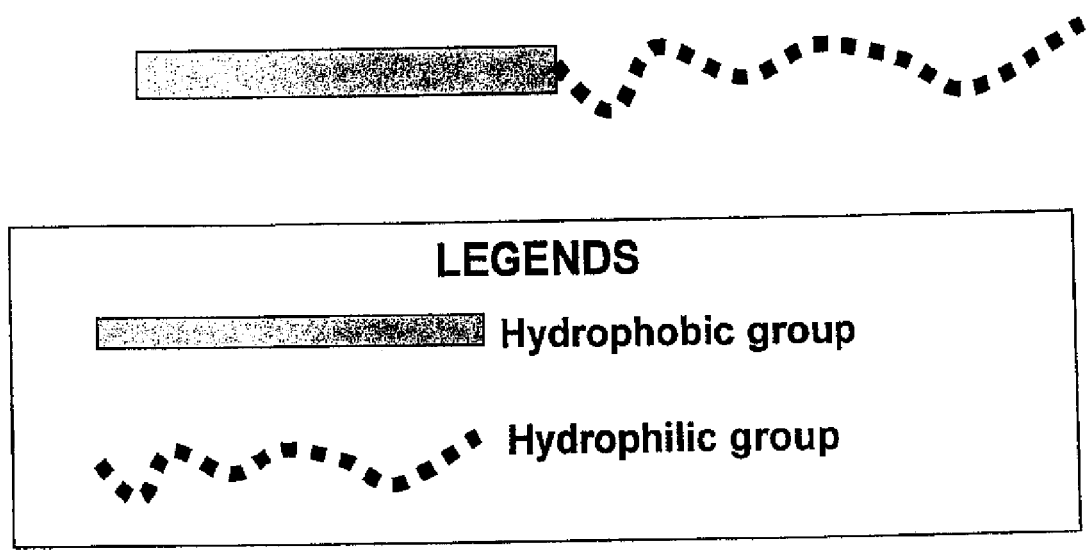
FIG. 3 depicts a non-limiting diagram of one of the components of the present invention comprising a hydrophobic group (H; light grey rectangle) linked to a hydrophilic group (P; dashed black wavy line). This component can be used, for example, to provide aqueous solubility to the supermolecular structure depicted in FIG. 2 by way of FIG. 4.
Figure 4:
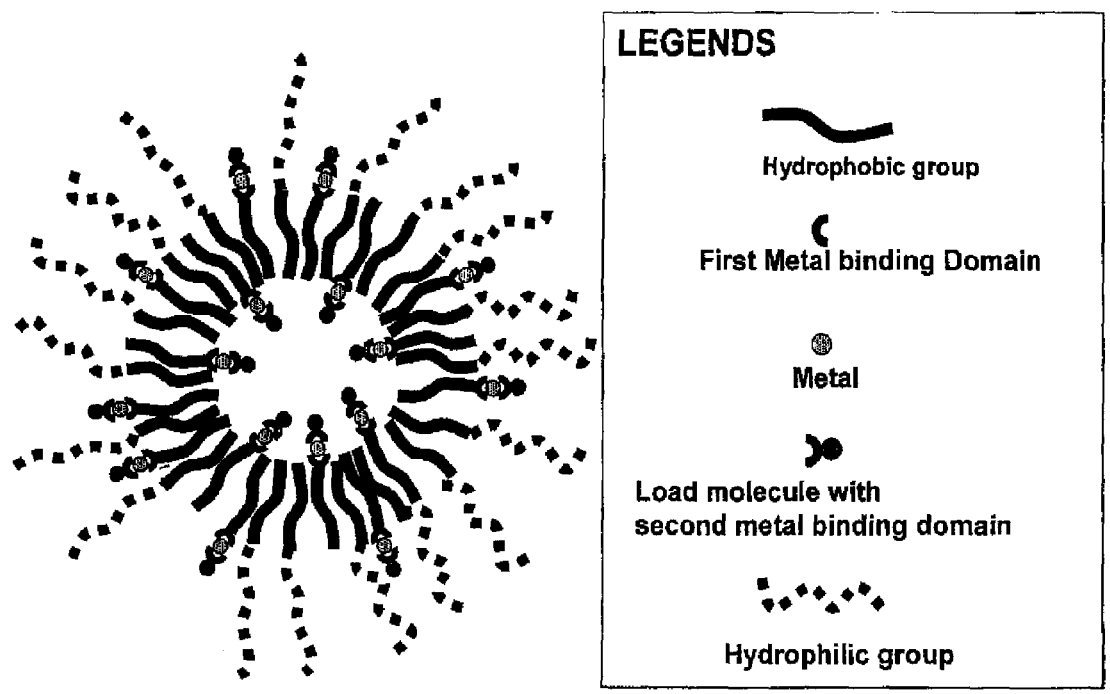
FIG. 4 depicts a non-limiting diagram of a supermolecular structure of one of the embodiments of the present invention comprising a carrier. The carrier comprises a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). The composition further comprises an amphipathic constituent comprising a hydrophobic group H linked to a hydrophilic group (P; dashed black wavy line). In the figure is a two-dimensional diagram of one of the arrangements of the mixture of the components depicting the formation of a supermolecular structure which is only one of many possible supermolecular structures of the mixed components that may form in the composition.

In another embodiment, the carrier comprises a hydrophobic group linked to a FMBD. The FMBD may chelate a metal ion, which is further chelated by a SMBD linked to an agent of interest. This composition may further include an amphipathic constituent comprising a hydrophobic group and a hydrophilic group. In one embodiment, an amphipathic constitutent is illustrated schematically in FIG. 3. In one embodiment, a composition comprising (1) an amphipathic constituent and (2) a metal ion, a SMBD linked to an agent, and a carrier comprising a hydrophobic group linked to a FMBD is illustrated in FIG. 4. In some embodiments, the amphipathic constituent is a "distinct chemical entity". The use of the term "distinct chemical entity" in the present specification means not covalently bonded nor coordinated, as in metal coordination, to the other components of the mixture. For example, the composition may comprise a component A having a hydrophobic group covalently linked to a FMBD which chelates a metal ion which is then further chelated by a SMBD covalently linked to an agent, and a component B having a hydrophobic group covalently linked to a hydrophilic group. When component A and component B are mixed in solution, they will form composition C that may or may not form a supermolecular structure such as a reverse micelle, micelle or microemulsion. In this case, component A and component B are distinct chemical entities mixed together to form composition C. Exemplary supermolecular structures, such as reverse micelles, micelles or microemulsions, are described in detail in U.S. Patent Application Publication No. 2003/0224974 which is hereby incorporated by reference. For the purpose of clarity, this composition can be represented by [L-SMBD-Me-FMBD-H] plus [H-P]; where H=hydrophobic group: Me=metal ion: FMBD=first metal binding domain; SMBD=second metal binding domain: L=agent or load molecule: P=hydrophilic group.

Figure 5:
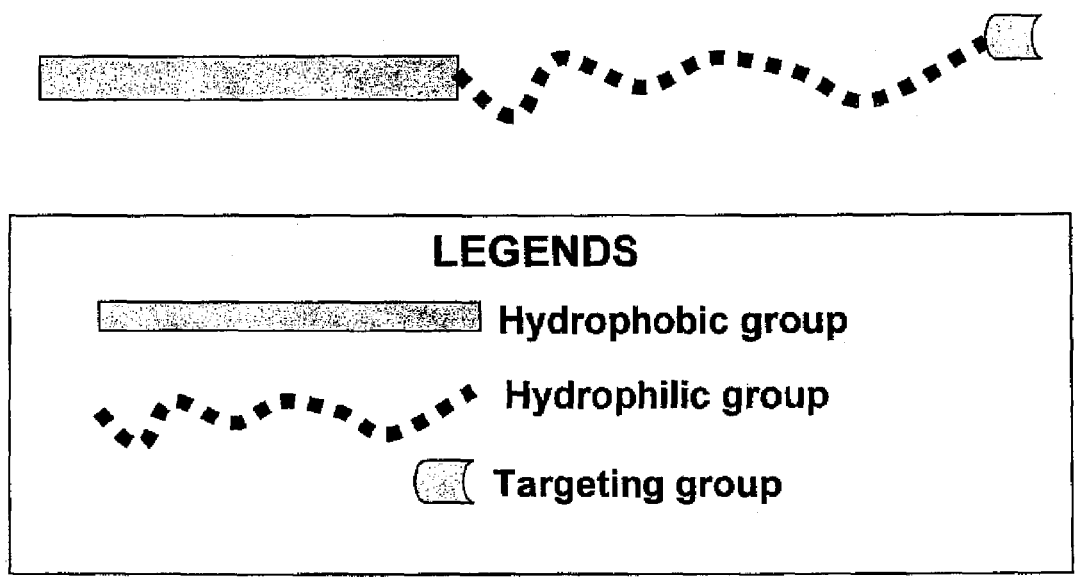
FIG. 5 depicts a non-limiting diagram of a component of various embodiments of the present invention comprising an amphipathic constituent linked to a targeting group (T; elongated grey half-moon). The amphipathic constituent comprises a hydrophobic group (H; light grey rectangle) and a hydrophilic group (P; dashed black wavy line). This component can be used, for example, to provide aqueous solubility and targeting properties to a supermolecular structure depicted by, for example, a diagram in FIG. 6.
Figure 6:
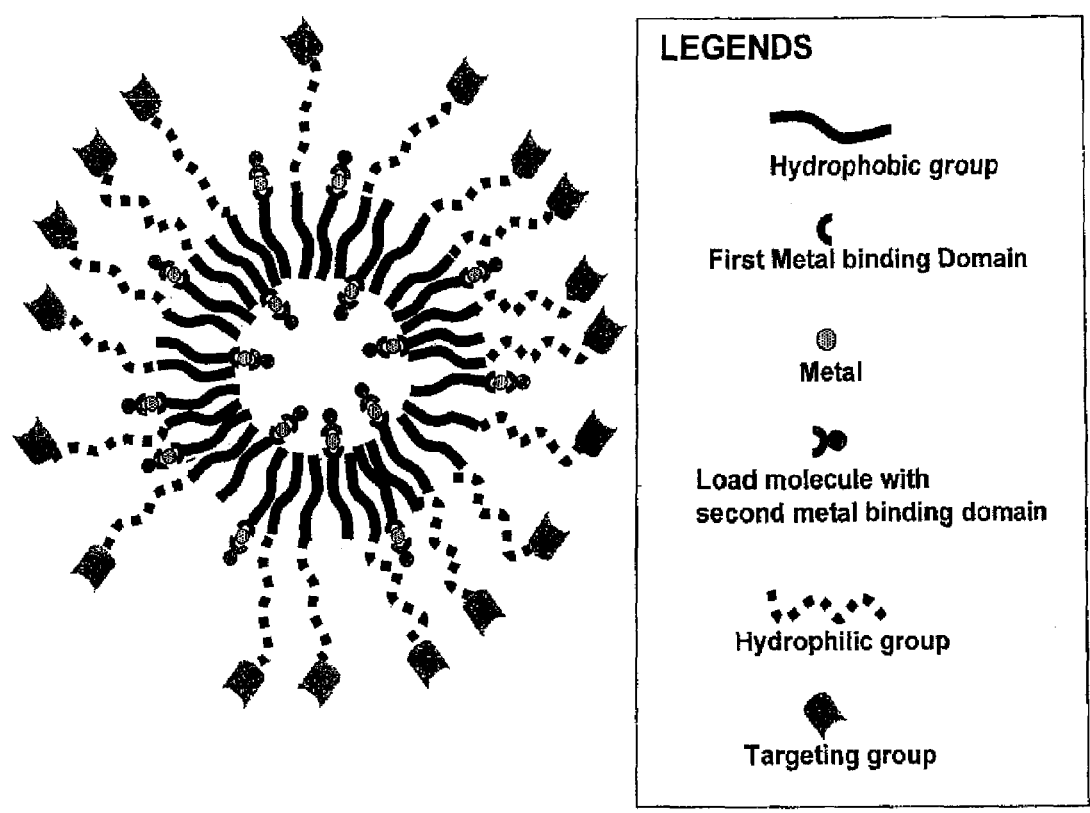
FIG. 6 depicts a non-limiting diagram of a supermolecular structure of one of the embodiments of the present invention comprising a carrier. The carrier comprises a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). The composition further comprises an amphipathic constituent linked to a targeting group (T; elongated grey half-moon). In the figure is a two-dimensional diagram of an arrangement of the mixture of the components depicting the formation of a supermolecular structure which is only one of many possible supermolecular structures of the mixed components that may form in an aqueous environment. Another supermolecular structure (one of many possible supermolecular structures) is where all the Ls are inside the supermolecular structure which can be accomplished, for example, by sequential rather than simultaneous addition of each component into solvents of specific composition.

In another embodiment, the carrier comprises a hydrophobic group linked to a FMBD. The FMBD may chelate a metal ion, which is further chelated by a SMBD linked to an agent of interest. This composition may further include an amphipathic constituent linked to a targeting group. In one embodiment, an amphipathic constituent linked to a targeting group is illustrated schematically in FIG. 5. The hydrophilic group of the amphipathic constituent may have a first end and a second end. In some embodiments, the first end of the hydrophilic group of the amphipathic constituent is linked to the hydrophobic group of the amphipathic constituent, while the second end is linked to a targeting group as illustrated, for example, in FIG. 5. The amphipathic constituent linked to a targeting group may be a distinct chemical entity. One example of a composition comprising (1) an amphipathic constituent linked to a targeting group and (2) a metal ion, a SMBD linked to an agent, and a carrier comprising a hydrophobic group linked to a FMBD is illustrated in FIG. 6. For the purpose of clarity, this composition can be represented by [L-SMBD-Me-FMBD-H] plus [H-P-T]; where H=hydrophobic group: Me=metal ion: FMBD=first metal binding domain; SMBD=second metal binding domain: L=agent or load molecule: P=hydrophilic group: T=targeting group.

Figure 7:
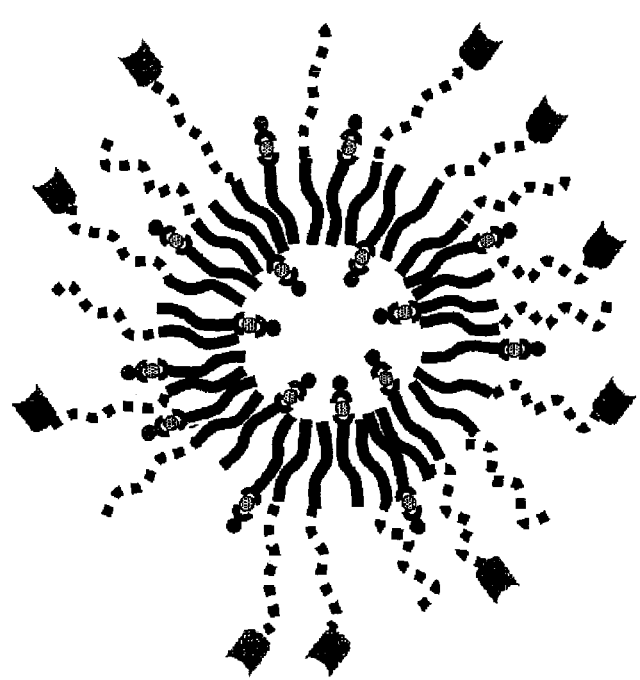
FIG. 7 depicts a non-limiting diagram of one of the embodiments of the present invention comprising a carrier. The carrier comprises a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). The composition further comprises an amphipathic constituent comprising a hydrophobic group (H; light grey rectangle) linked to a hydrophilic group (P; dashed black wavy line). The composition further comprises an amphipathic constituent linked to a targeting group (T; elongated grey half-moon). In the figure is a two-dimensional diagram of the arrangement of the components in the mixture depicting the formation of a supermolecular structure which is only one of many possible supermolecular structures of the mixed components that may form in an aqueous environment. Another supermolecular structure (one of many possible supermolecular structures) is where all the Ls are inside the supermolecular structure which can be accomplished, for example, by the sequential addition (rather than simultaneous) of each component into solvent of specific composition.

In another embodiment, the carrier comprises a hydrophobic group linked to a FMBD. The FMBD may chelate a metal ion, which is further chelated by a SMBD linked to an agent of interest. This composition may further include an amphipathic constituent. The amphipathic constituent may be a distinct chemical entity. This composition may further include an amphipathic constituent linked to a targeting group. The amphipathic constituent linked to a targeting group may be a distinct chemical entity. One example of a composition comprising (1) an amphipathic constituent (2) an amphipathic constituent linked to a targeting group and (2) a metal ion, a SMBD linked to an agent, and a carrier comprising a hydrophobic group linked to a FMBD is illustrated in FIG. 7. For the purpose of clarity, this composition can be represented by [L-SMBD-Me-FMBD-H] plus [H-P] plus [H-P-T]; where H=hydrophobic group: Me=metal ion: FMBD=first metal binding domain; SMBD=second metal binding domain: L=agent or load molecule: P=hydrophilic group: T=targeting group.

Figure 8:
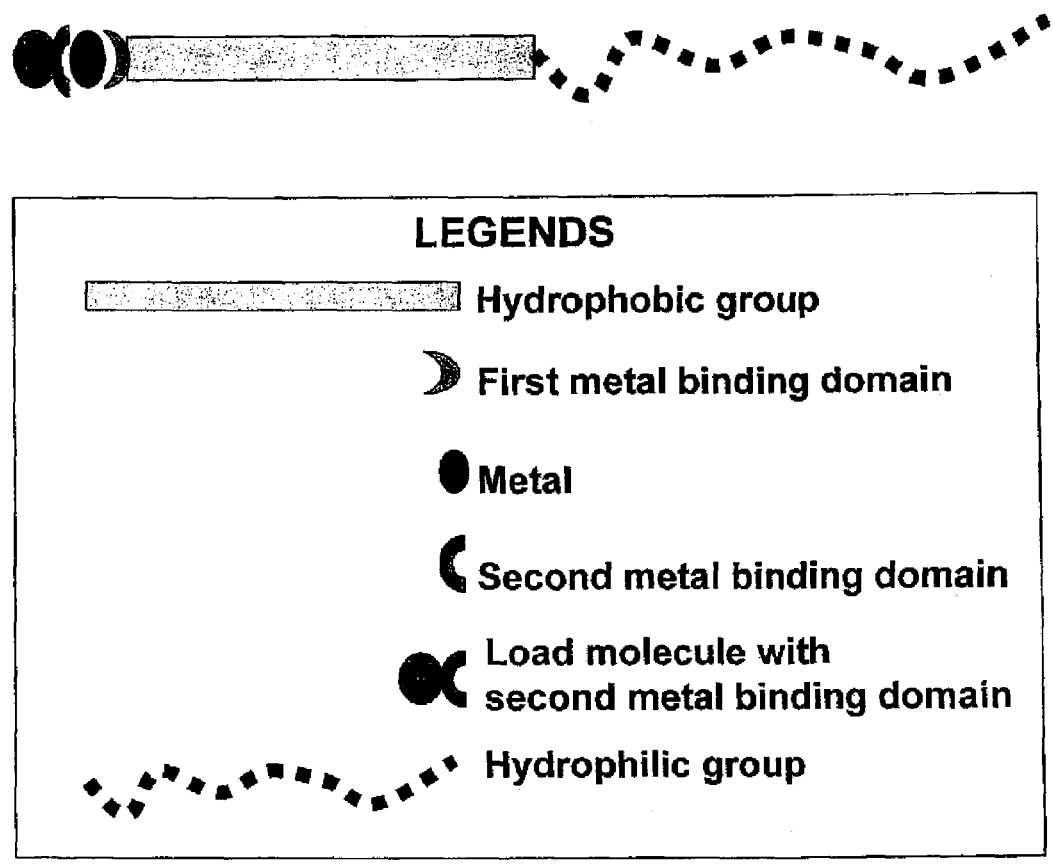
FIG. 8 depicts a non-limiting diagram of a component of various embodiments of the present invention comprising a carrier. The carrier comprises a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). This component can form a supermolecular structure such as that depicted in FIG. 9.
Figure 9:
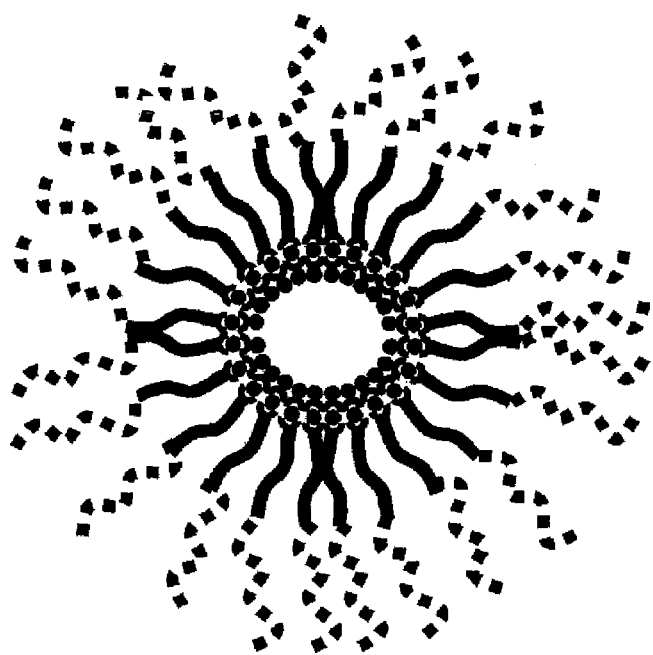
FIG. 9 depicts a non-limiting diagram of a supermolecular structure of one of the embodiments of the present invention comprising a carrier. The carrier comprises a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). In the figure is a two-dimensional diagram of an arrangement of the components depicting the formation of a supermolecular structure that is one of many possible arrangements of the components that may form.
Figure 9:
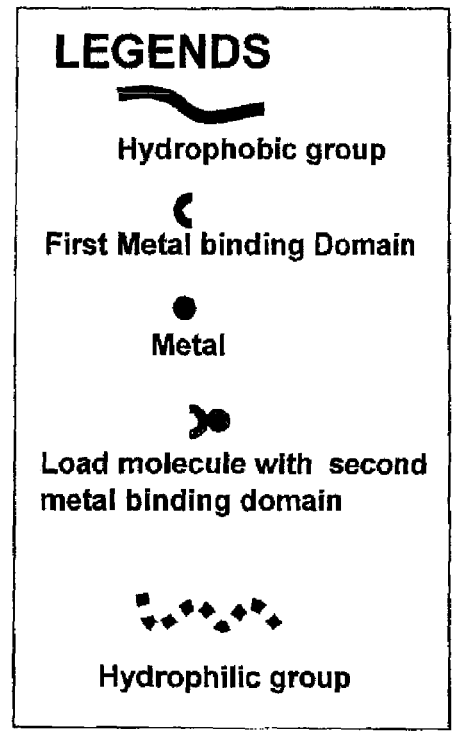

In another embodiment, the carrier comprises a hydrophobic group, a FMBD, and a hydrophilic group. The FMBD chelates a metal ion, which is further chelated by a SMBD linked to an agent of interest. The hydrophobic group of the carrier may have a first end and a second end. The first end of the hydrophobic group of the carrier may be linked to the FMBD and the second end of the hydrophobic group may be linked to a hydrophilic group as illustrated, for example, in FIG. 8. One example of a composition comprising a metal ion, a SMBD linked to an agent, and a carrier comprising a hydrophobic group, a FMBD, and a hydrophilic group is illustrated in FIG. 9. For the purpose of clarity, this composition can be represented by [L-SMBD-Me-FMBD-H-P]; where H=hydrophobic group: Me=metal ion: FMBD=first metal binding domain; SMBD=second metal binding domain: L=agent or load molecule: P=hydrophilic group.

Figure 10:
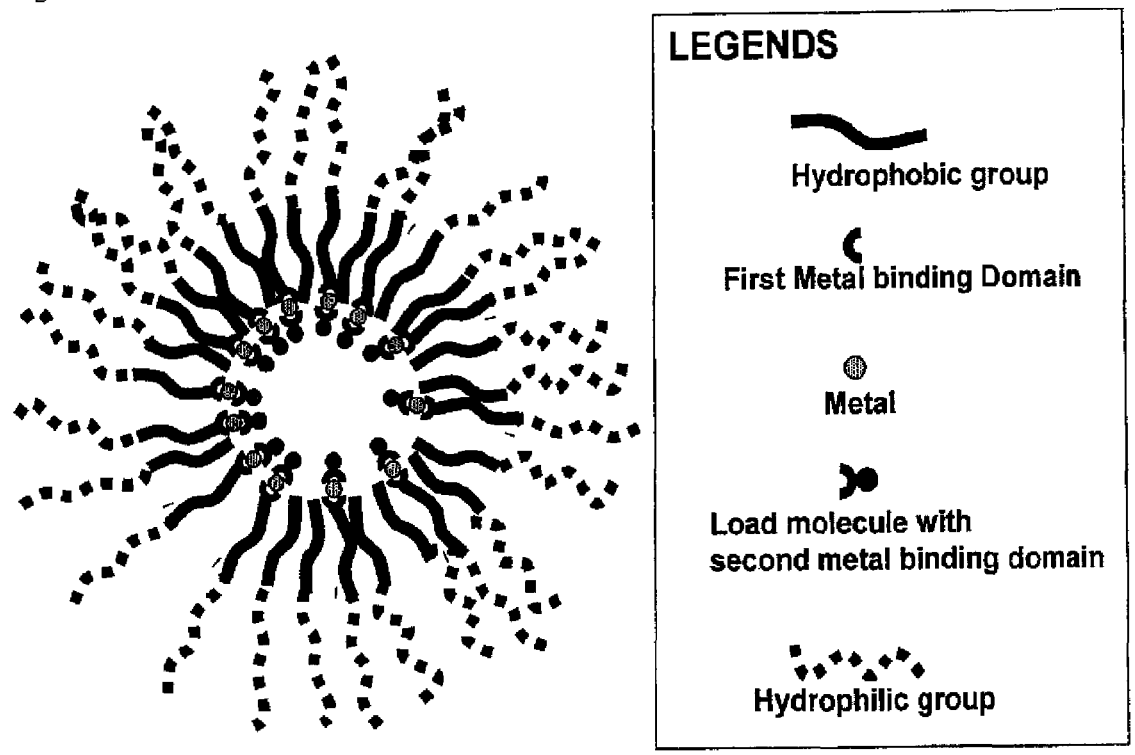
FIG. 10 depicts a non-limiting diagram of a supermolecular structure of one of various embodiments of the present invention comprising a carrier. The carrier comprises a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). This composition further comprises an amphipathic constituent comprising a hydrophobic group H linked to a hydrophilic group (P; dashed black wavy line). In the figure is a two-dimensional diagram of an arrangement of the mixture of the components depicting the formation of a supermolecular structure which is only one of many possible supermolecular structures of the mixed components that may form in an aqueous environment.

In another embodiment, the carrier comprises a hydrophobic group, a FMBD, and a hydrophilic group. The FMBD chelates a metal ion, which is further chelated by a SMBD linked to an agent of interest. The hydrophobic group of the carrier may have a first end and a second end. The first end of the hydrophobic group of the carrier may be linked to the FMBD and the second end of the hydrophobic group may be linked to a hydrophilic group as illustrated, for example, in FIG. 8. The composition may further include an amphipathic constituent. The amphipathic constituent may be a distinct chemical entity. One example of a composition comprising (1) a metal ion, a SMBD linked to an agent, and a carrier comprising a hydrophobic group, a FMBD, and a hydrophilic group and (2) an amphipathic constituent is illustrated in FIG. 10. For the purpose of clarity, this composition can be represented by [L-SMBD-Me-FMBD-H-P] plus [H-P]; where H=hydrophobic group: Me=metal ion: FMBD=first metal binding domain; SMBD=second metal binding domain: L=agent or load molecule: P=hydrophilic group.

Figure 11:
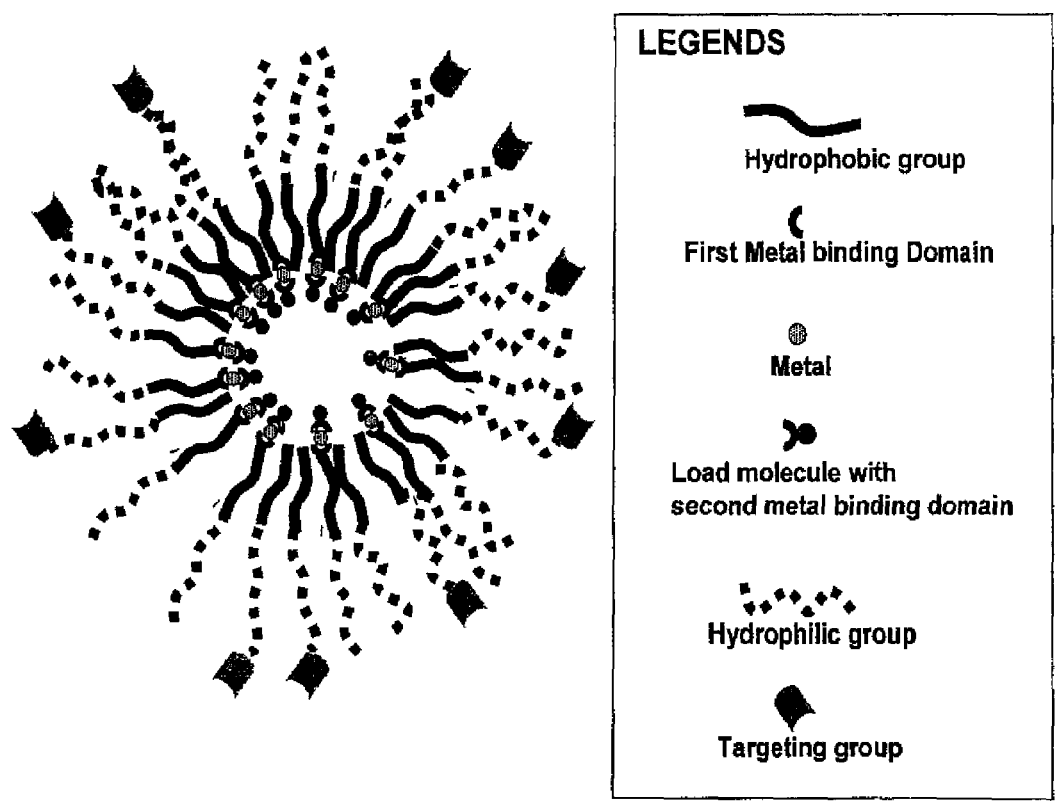
FIG. 11 depicts a non-limiting diagram of a supermolecular structure of one of various embodiments of the present invention comprising a carrier comprising a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). This composition further comprises an amphipathic constituent comprising a hydrophobic group H linked to a hydrophilic group (P; dashed black wavy line). This composition further comprises an amphipathic constituent linked to a targeting group (T; elongated grey half-moon). In the figure is a two-dimensional diagram of an arrangement of the mixture the components depicting the formation of a supermolecular structure which is only one of many possible arrangements of the mixed components that may form in an aqueous environment.
Figure 12:
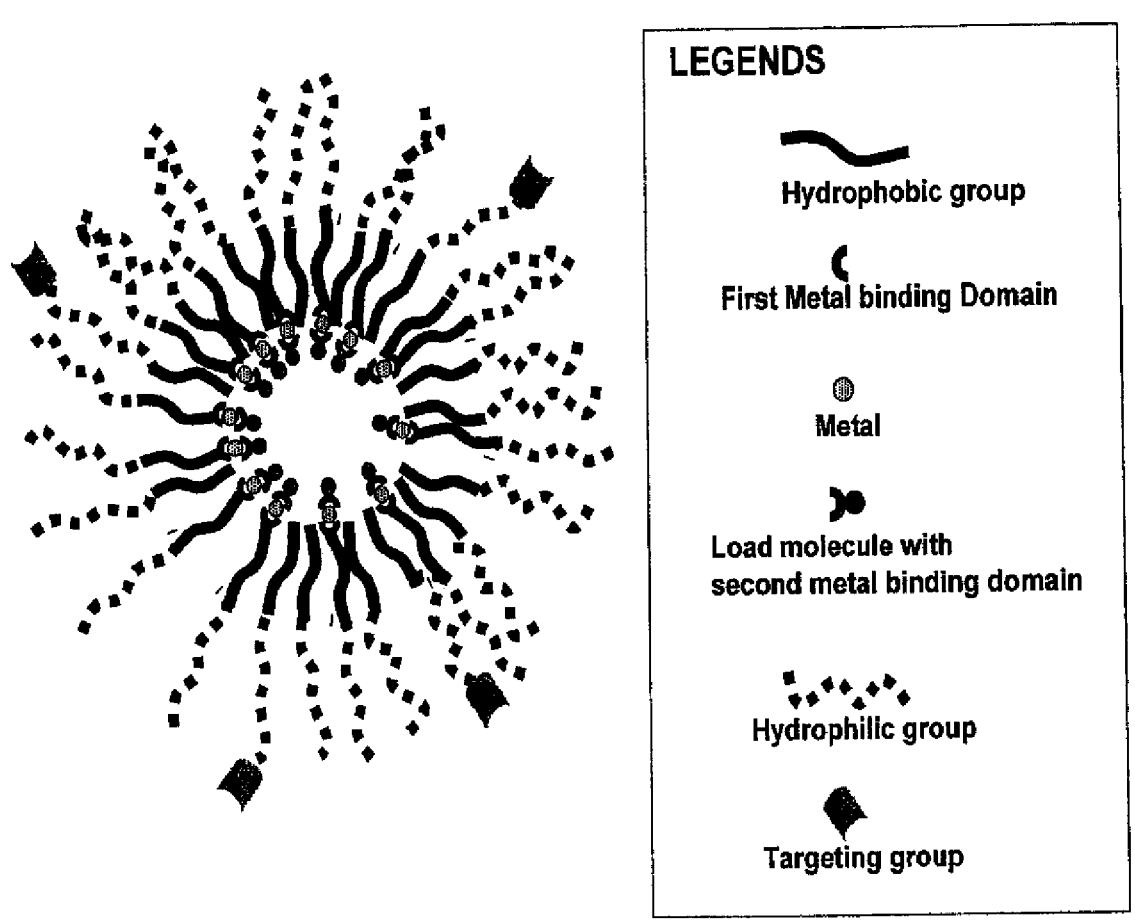
FIG. 12 depicts a non-limiting diagram of a supermolecular structure of one of various embodiments of the present invention comprising a carrier comprising a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). This composition further comprises an amphipathic constituent comprising a hydrophobic group H linked to a hydrophilic group (P; dashed black wavy line). This composition further comprises an amphipathic constituent linked to a targeting group (T; elongated grey half-moon). In the figure is a two-dimensional diagram of an arrangement of the mixture the components depicting the formation of a supermolecular structure which is only one of many possible arrangements of the mixed components that may form in an aqueous environment.

In another embodiment, the carrier comprises a hydrophobic group, a FMBD, and a hydrophilic group. The FMBD chelates a metal ion, which is further chelated by a SMBD linked to an agent of interest. The hydrophobic group of the carrier may have a first end and a second end. The first end of the hydrophobic group of the carrier may be linked to the FMBD and the second end of the hydrophobic group may be linked to a hydrophilic group as illustrated, for example, in FIG. 8. The composition may further include an amphipathic constituent. The amphipathic constituent may be a distinct chemical entity. The composition may further include an amphipathic constituent linked to a targeting group. The amphipathic constituent linked to a targeting group may be a distinct chemical entity. In some embodiments, compositions comprising (1) a metal ion, a SMBD linked to an agent, and a carrier comprising a hydrophilic group, a FMBD, and a hydrophobic group and (2) an amphipathic constituent and (3) an amphipathic constituent linked to a targeting group are illustrated in FIGS. 11 and 12. For the purpose of clarity, this composition can be represented by [L-SMBD-Me-FMBD-H-P] plus [H-P] plus [H-P-T]; where H=hydrophobic group: Me=metal ion: FMBD=first metal binding domain; SMBD=second metal binding domain: L=agent or load molecule: P=hydrophilic group and T=targeting group.

Figure 13:
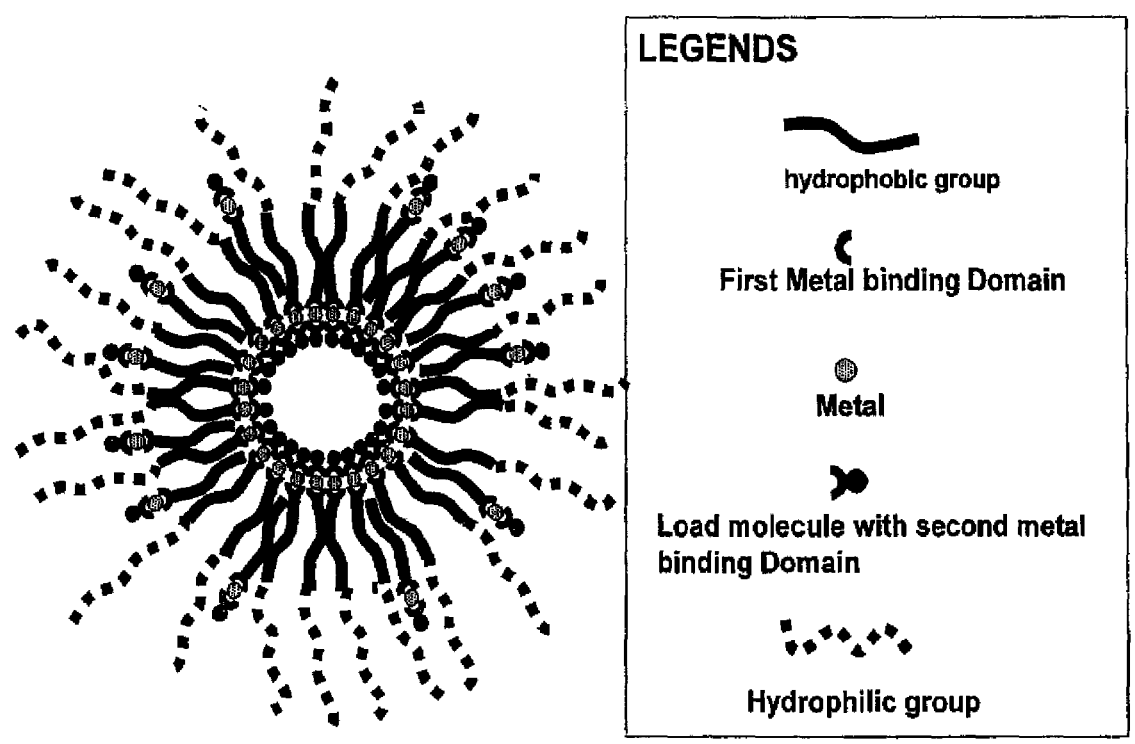
FIG. 13 depicts a non-limiting diagram of a supermolecular structure of one of various embodiments of the present invention comprising a carrier comprising a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). This composition further comprises a second carrier comprising a hydrophobic group (H; light grey rectangle), a third metal binding domain (TMBD; half-moon dark grey) linked to H, and a hydrophilic group (P; dashed black wavy line). A metal ion (Me; black oval) is chelated by the TMBD and a second metal binding domain (SMBD; half circle dark grey). The second metal binding domain is linked to or part of the agent (L; dark grey circle with X inside). In the figure is a two-dimensional diagram of an arrangement of the mixture of the components depicting the formation of a supermolecular structure which is only one of many possible supermolecular structures of the mixed components that may form in an aqueous environment.

In another embodiment, the carrier comprises a hydrophobic group linked to a FMBD. The FMBD chelates a metal ion, which is further chelated by a SMBD linked to an agent of interest. The composition may further include a second carrier. The second carrier may comprise a hydrophobic group, a third metal binding domain (TMBD), and a hydrophilic group. The hydrophobic group of the second carrier may have a first end and a second end. The first end of the hydrophobic group of the second carrier may be linked to the TMBD and the second end of the hydrophobic group may be linked to a hydrophilic group as illustrated in FIG. 8. The second carrier comprising a hydrophobic group linked to a TMBD and a hydrophilic group may be a distinct chemical entity. One example of a composition comprising (1) a metal ion, a SMBD linked to an agent, and a carrier comprising a hydrophobic group linked to a FMBD and (2) a second carrier comprising a hydrophobic group, a third metal binding domain (TMBD) and a hydrophilic group is illustrated in FIG. 13. For the purpose of clarity, this composition can be represented by [L-SMBD-Me-FMBD-H] plus [L-SMBD-Me-TMBD-H-P]; where H=hydrophobic group: Me=metal ion: FMBD=first metal binding domain; SMBD=second metal binding domain: L=agent or load molecule: P=hydrophilic group: TMBD=third metal binding domain.

Figure 14:
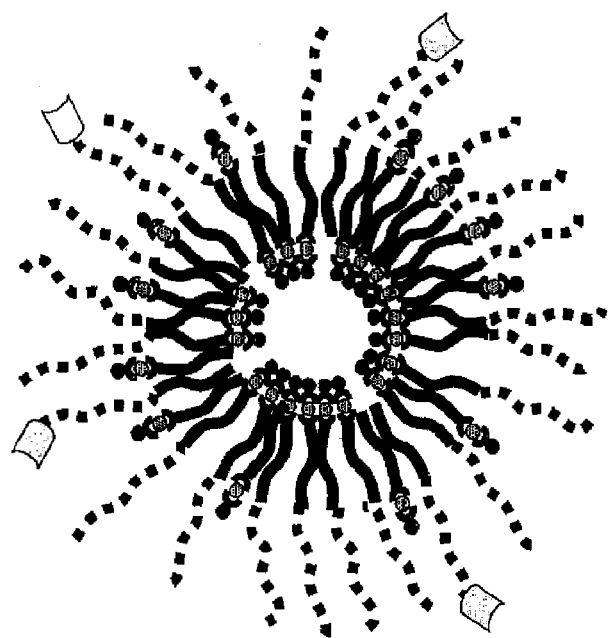
FIG. 14 depicts a non-limiting diagram of a supermolecular structure of one of various embodiments of the present invention comprising a carrier comprising a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). This composition further comprises a second carrier comprising a hydrophobic group (If; light grey rectangle), a third metal binding domain (TMBD; half-moon dark grey) linked to H, and a hydrophilic group (P; dashed black wavy line). A metal ion (Me; black oval) is chelated by the TMBD and a second metal binding domain (SMBD; half circle dark grey). The second metal binding domain is linked to or part of the agent (L; dark grey circle with X inside). This composition further comprises an amphiphatic constituent linked to a targeting group (T; elongated grey half-moon). In the figure is a two-dimensional diagram of an arrangement of the mixture of the components depicting the formation of a supermolecular structure which is only one of many possible supermolecular structures of the mixed components that may form in an aqueous environment.

In another embodiment, the carrier comprises a hydrophobic group linked to a FMBD. The FMBD chelates a metal ion, which is further chelated by a SMBD linked to an agent of interest. The composition may further include a second carrier. The second carrier may comprise a hydrophobic group, a third metal binding domain (TMBD), and a hydrophilic group. The hydrophobic group of the second carrier may have a first end and a second end. The first end of the hydrophobic group of the second carrier may be linked to the TMBD and the second end of the hydrophobic group may be linked to a hydrophilic group as illustrated in FIG. 8. The second carrier comprising a hydrophobic group linked to a TMBD and a hydrophilic group may be a distinct chemical entity. The composition may further include an amphipathic constituent linked to a targeting group. The amphipathic constituent linked to a targeting group may be a distinct chemical entity. One example of a composition comprising (1) a metal ion, a SMBD linked to an agent, and a carrier comprising a hydrophobic group linked to a FMBD and (2) a second carrier comprising a hydrophobic group, a third metal binding domain (TMBD) and a hydrophilic group and (3) an amphipathic constituent linked to a targeting group is illustrated in FIG. 14. For the purpose of clarity, this composition can be represented by [L-SMBD-Me-FMBD-H] plus [L-SMBD-Me-TMBD-H-P] plus [H-P-T]; where H=hydrophobic group: Me <<metal ion: FMBD=first metal binding domain; SMBD=second metal binding domain: L=agent or load molecule: P=hydrophilic group: TMBD=third metal binding domain.

Figure 15:
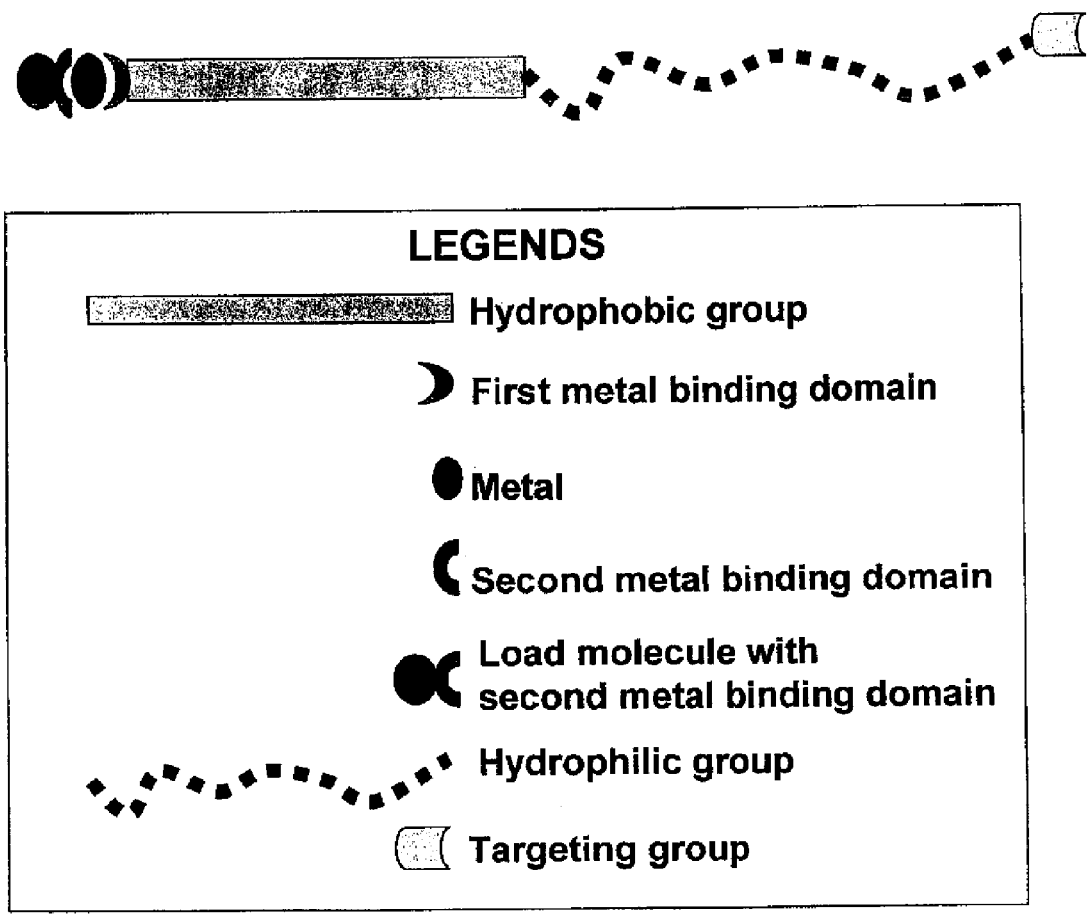
FIG. 15 depicts a non-limiting diagram of a component of various embodiments of the present invention comprising a carrier comprising a hydrophobic group (H; light grey rectangle), a first metal binding domain (FMBD; half-moon dark grey) linked to H, a hydrophilic group (P; dashed black wavy line), and a targeting group (T; elongated grey half-moon). A metal ion (Me; black oval) is chelated by the FMBD and a second metal binding domain (SMBD; half circle dark grey). The second metal binding domain is linked to or part of the agent (L; dark grey circle with X inside). This component can form a supermolecular structure, for example, as depicted in FIG. 16.
Figure 16:
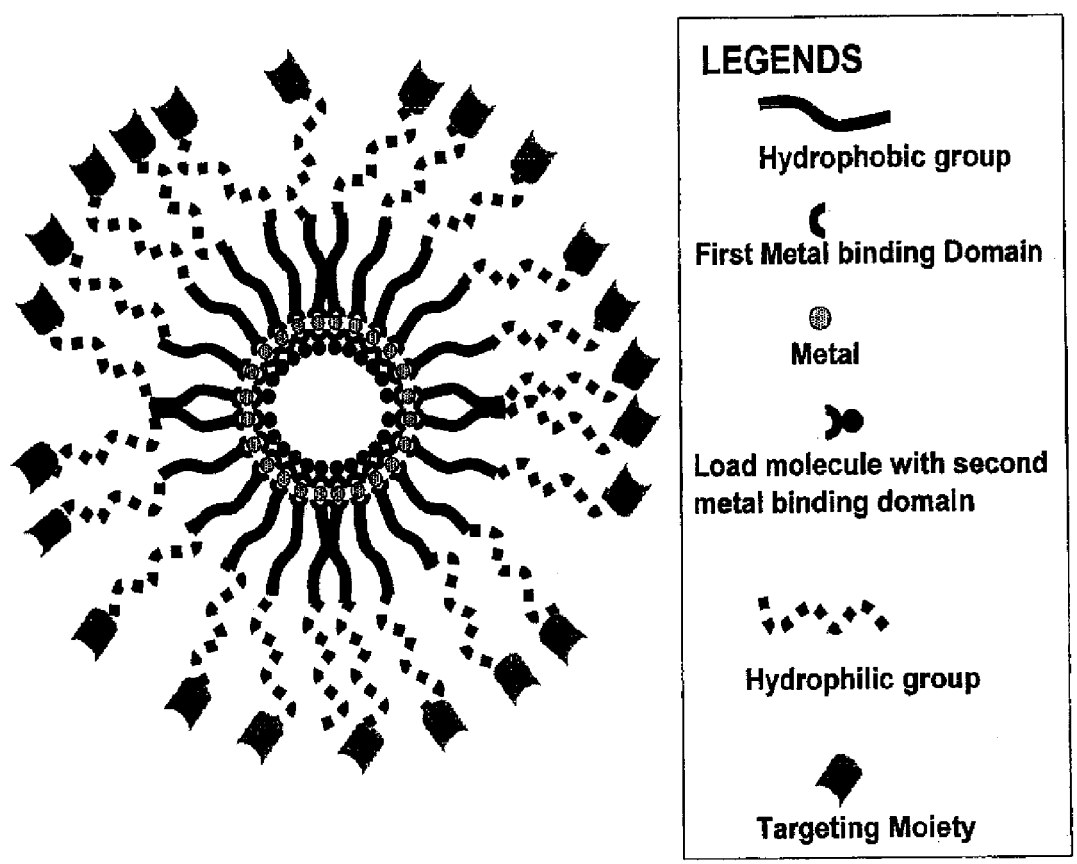
FIG. 16 depicts a non-limiting diagram of a supermolecular structure of one of the embodiments of the present invention comprising a carrier. The carrier comprises a hydrophobic group (H; light grey rectangle), a first metal binding domain (FMBD; half-moon dark grey) linked to H, a hydrophilic group (I); dashed black wavy line), and a targeting group (T; elongated grey half-moon). A metal ion (Me; black oval) is chelated by the FMBD and a second metal binding domain (SMBD; half circle dark grey). The second metal binding domain is linked to or part of the agent (L; dark grey circle with X inside). In the figure is a two-dimensional diagram of an arrangement of the composition depicting the formation of a supermolecular structure that is one of many possible supermolecular structures of the composition.

In another embodiment, the composition includes a carrier. The carrier comprises a hydrophobic group, a FMBD, a hydrophilic group and a targeting group. The FMBD chelates a metal ion. The metal ion is further chelated by a SMBD linked to an agent. The hydrophobic group of the carrier has a first end and second end. The first end of the hydrophobic group of the carrier is linked to the FMBD. The second end of the hydrophobic group of the carrier may be linked to a hydrophilic group as illustrated schematically in FIG. 15. The hydrophilic group may have a first end and second end. The first end of the hydrophilic group may be linked to the hydrophobic group of the carrier, and the second end of the hydrophilic group may be linked to a targeting group. One example of a composition comprising (1) a metal ion, a SMBD linked to an agent, and a carrier comprising a hydrophobic group, a FMBD, a hydrophilic group and a targeting group is illustrated in FIG. 16. For the purpose of clarity, this composition can be represented by [L-SMBD-Me-FMBD-H-P-T]; where H=hydrophobic group: Me=metal ion: FMBD=first metal binding domain; SMBD=second metal binding domain: L=agent or load molecule: P=hydrophilic group: T=targeting group.

Figure 17:
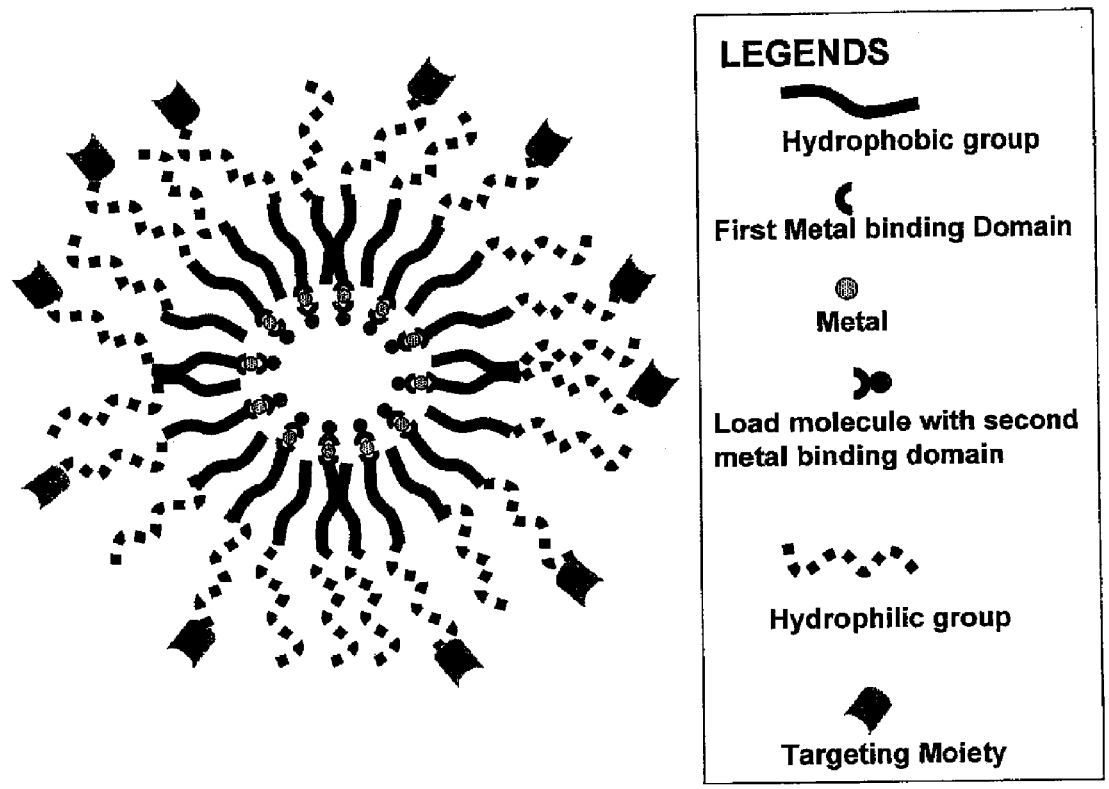
FIG. 17 depicts a non-limiting diagram of a supermolecular structure of one of the embodiments of the present invention comprising a carrier comprising a hydrophobic group (H; light grey rectangle), a first metal binding domain (FMBD; half-moon dark grey) linked to H, a hydrophilic group (P; dashed black wavy line), and a targeting group (T; elongated grey half-moon). A metal ion (Me; black oval) is chelated by the FMBD and a second metal binding domain (SMBD; half circle dark grey). The second metal binding domain is linked to or part of the agent (L; dark grey circle with X inside). This composition further comprises an amphipathic constituent. In the figure is a two-dimensional diagram of an arrangement of the mixture of the components depicting the formation of a supermolecular structure which is only one of many possible supermolecular structures of the mixed components that may form in an aqueous environment.

In another embodiment, the composition includes a carrier. The carrier comprises a hydrophobic group, a FMBD, a hydrophilic group and a targeting group. The FMBD chelates a metal ion. The metal ion is further chelated by a SMBD linked to an agent. The hydrophobic group of the carrier has a first end and second end. The first end of the hydrophobic group of the carrier is linked to the FMBD. The second end of the hydrophobic group of the carrier may be linked to a hydrophilic group as illustrated schematically in FIG. 15. The hydrophilic group may have a first end and second end. The first end of the hydrophilic group may be linked to the hydrophobic group of the carrier, and the second end of the hydrophilic group may be linked to a targeting group. This composition may further include an amphipathic constituent. The amphipathic constituent may be a distinct chemical entity. One example of a composition comprising (1) a metal ion, a SMBD linked to an agent, and a carrier comprising a hydrophobic group, a FMBD, a hydrophilic group, and a targeting group and (2) an amphipathic constituent is illustrated in FIG. 17. For the purpose of clarity, this composition can be represented by [L-SMBD-Me-FMBD-H-P-T] plus [H-P]; where H=hydrophobic group: Me=metal ion: FMBD=first metal binding domain; SMBD=second metal binding domain: L=agent or load molecule: P=hydrophilic group: T=targeting group.

Figure 18:
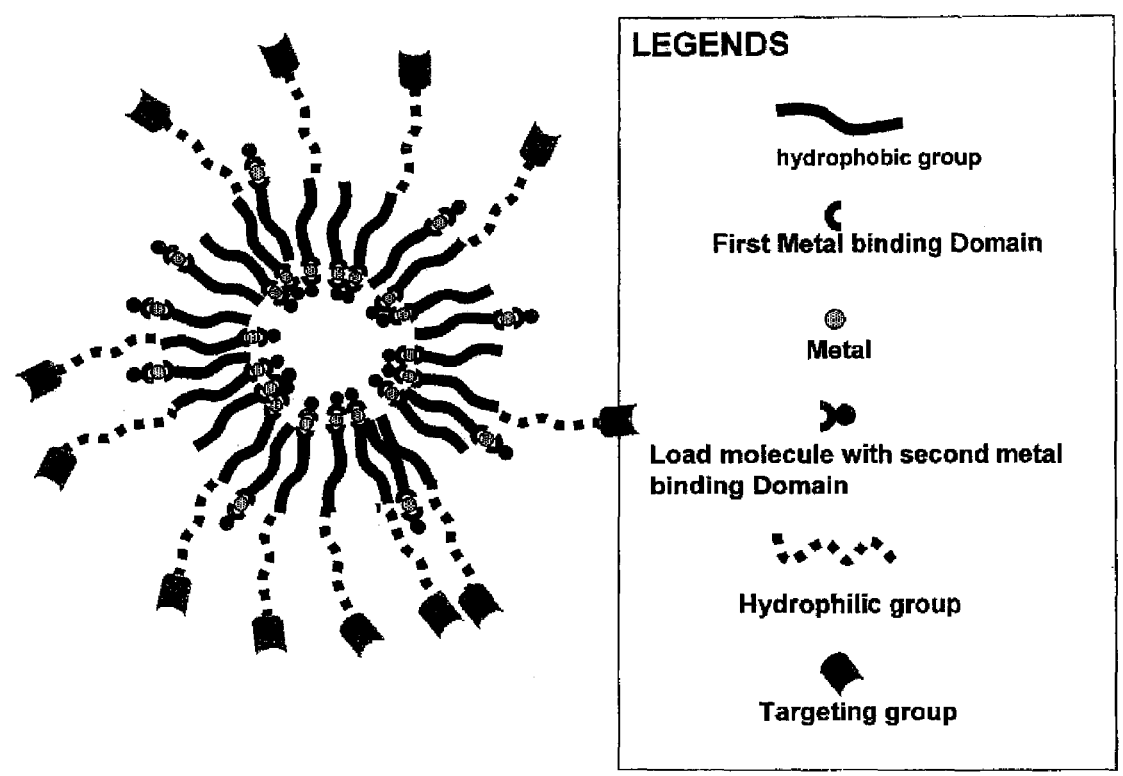
FIG. 18 depicts a non-limiting diagram of a supermolecular structure of one of the embodiments of the present invention comprising a carrier comprising a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). The composition further comprises a second carrier comprising a hydrophobic group (H; light grey rectangle), a third metal binding domain (TMBD; half-moon dark grey) linked to H, a hydrophilic group (P; dashed black wavy line), and a targeting group (T; elongated grey half-moon). A metal ion (Me; black oval) is chelated by the TMBD and a second metal binding domain (SMBD; half circle dark grey). The second metal binding domain is linked to or part of the agent (L; dark grey circle with X inside). In the figure is a two-dimensional diagram of an arrangement of the mixture of the components depicting the formation of a supermolecular structure which is only one of many possible supermolecular structures of the composition that may form in an aqueous environment.
Figure 19:
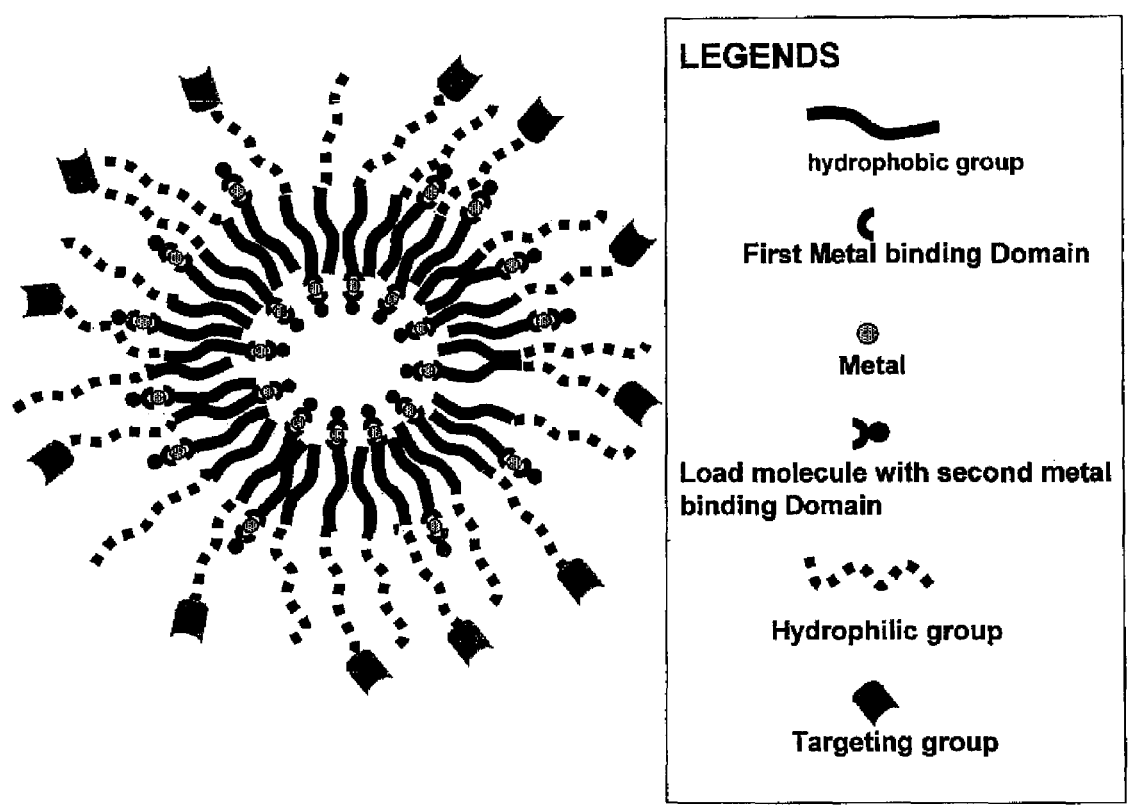
FIG. 19 depicts a non-limiting diagram of a supermolecular structure of one of the embodiments of the present invention comprising a carrier comprising a hydrophobic group (H; light grey rectangle) and a first metal binding domain (FMBD; half-moon dark grey) linked to H. A metal ion (Me; black oval) is chelated by the FMBD and a second metal binding domain (SMBD; half circle dark grey). The second metal binding domain is linked to or part of the agent (L; dark grey circle with X inside). The composition further comprises a second carrier comprising a hydrophobic group (H; light grey rectangle), a third metal binding domain (TMBD; half-moon dark grey) linked to H, a hydrophilic group (P; dashed black wavy line), and a targeting group (T; elongated grey half-moon). A metal ion (Me; black oval) is chelated by the TMBD and a second metal binding domain (SMBD; half circle dark grey). The second metal binding domain is linked to or part of the agent (L; dark grey circle with X inside). The composition further comprises an amphipathic constituent. The amphipathic constituent comprises a hydrophobic group H and a hydrophilic group P. In the figure is a two-dimensional diagram of an arrangement of the mixture of the components depicting the formation of a supermolecular structure which is only one of many possible supermolecular structures of the mixed components in an aqueous environment. Another supermolecular structure (one of many possible supermolecular structures) is where all the Ls are inside the supermolecular structure which can be accomplished by the sequence of additions and solvent composition during each addition.

In another embodiment, the composition includes a carrier comprising a hydrophobic group linked to a FMBD. The FMBD chelates a metal ion. The metal ion is further chelated by a SMBD linked to an agent. This composition may further include a second carrier. The second carrier may include a hydrophobic group, a third metal binding domain (TMBD), a hydrophilic group and a targeting group. The hydrophobic group of the second carrier may have a first end and second end. The hydrophilic group of the second carrier may have a first end and second end. The first end of the hydrophobic group of the second carrier may be linked to the third metal binding domain (TMBD) and the second end may be linked to the first end of the hydrophilic group. The second end of the hydrophilic group may be linked to the targeting group. The second carrier, metal ion, and second metal binding domain linked to an agent may be a distinct chemical entity. One example of a composition comprising (1) a metal ion, a SMBD linked to an agent, and a carrier comprising a hydrophobic group linked to a FMBD and (2) a second carrier comprising a hydrophobic group, a third metal binding domain (TMBD), a hydrophilic group and a targeting group is illustrated in FIG. 18. For the purpose of clarity, this composition can be represented by [L-SMBD-Me-TMBD-H-P-T] plus [L-SMBD-Me-FMBD-H]; where H=hydrophobic group: Me=metal ion: FMBD=first metal binding domain;

SMBD=second metal binding domain: L=agent or load molecule: P=hydrophilic group: T=targeting group: TMBD=third metal binding domain. This composition may further include an amphipathic constituent. The amphipathic constituent may be a distinct chemical entity. One example of a composition comprising (1) a metal ion, a SMBD linked to an agent, and a carrier comprising a hydrophobic group linked to a FMBD and (2) a second carrier comprising a hydrophobic group, a third metal binding domain (TMBD), a hydrophilic group and a targeting group and (3) an amphipathic constituent is illustrated in FIG. 19. For the purpose of clarity, this composition can be represented by [L-SMBD-Me-TMBD-H-P-T] plus [L-SMBD-Me-FMBD-H] plus [H-P]; where H=hydrophobic group: Me=metal ion: FMBD=first metal binding domain; SMBD=second metal binding domain: L=agent or load molecule: P=hydrophilic group: T=targeting group: TMBD=third metal binding domain.

Figure 20:
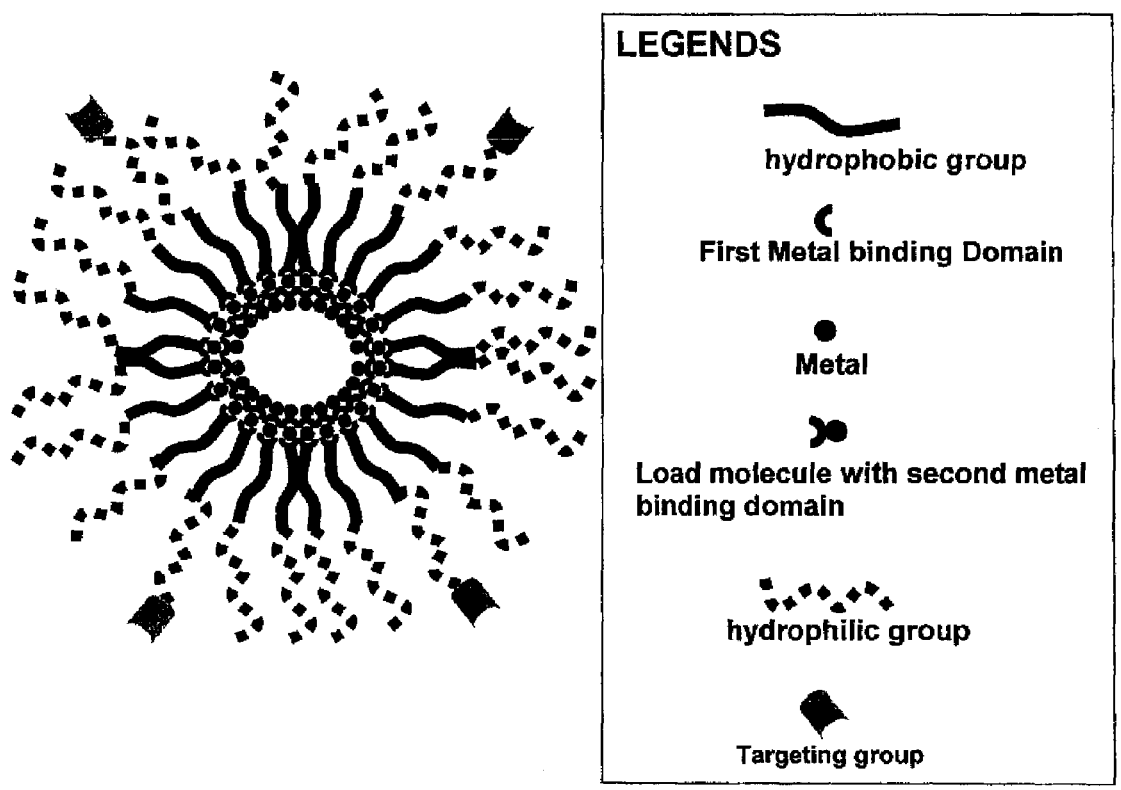
FIG. 20 depicts a non-limiting diagram of a supermolecular structure of one of the embodiments of the present invention comprising a carrier comprising a hydrophobic group (H; light grey rectangle), a first metal binding domain (FMBD; half-moon dark grey) linked to H, and a hydrophilic group (P; dashed black wavy line). A metal ion (Me; black oval) is chelated by the FMBD and a second metal binding domain (SMBD; half circle dark grey). The second metal binding domain is linked to or part of the agent (L; dark grey circle with X inside). The composition further comprises a second carrier comprising a hydrophobic group (H; light grey rectangle), a third metal binding domain (TMBD; half-moon dark grey) linked to H, a hydrophilic group (P; dashed black wavy line), and a targeting group (T; elongated grey half-moon). A metal ion (Me; black oval) is chelated by the TMBD and a second metal binding domain (SMBD; half circle dark grey). The second metal binding domain is linked to or part of the agent (L; dark grey circle with X inside). In the figure is a two-dimensional diagram of an arrangement of the mixture of the components depicting the formation of a supermolecular structure which is only one of many possible supermolecular structures of the mixed components that may form in an aqueous environment.

In another embodiment, the composition includes a carrier comprising a hydrophobic group, a FMBD, a hydrophilic group, and a targeting group. The FMBD chelates a metal ion. The metal ion is further chelated by a SMBD linked to an agent. The hydrophobic group of the carrier has a first end and second end. The first end of the hydrophobic group of the carrier is linked to the FMBD. The second end of the hydrophobic group of the carrier may be linked to a hydrophilic group. The hydrophilic group may have a first end and second end. The first end of the hydrophilic group may be linked to the hydrophobic group and the second end may be linked to the targeting group. This composition may further include a second carrier. The second carrier may include a hydrophobic group, a third metal binding domain (TMBD), and a hydrophilic group. The hydrophobic group of the second carrier may have a first end and a second end. The first end of the hydrophobic group of the second carrier may be linked to the third metal binding domain (TMBD) and the second end may be linked to the hydrophilic group of the second carrier. The second carrier, metal ion, and second metal binding domain linked to an agent may be a distinct chemical entity. One example of a composition comprising (1) a metal ion, a SMBD linked to an agent, and a carrier comprising a hydrophobic group, a FMBD, a hydrophilic group, and a targeting group and (2) a second carrier comprising a hydrophobic group, a TMBD, and a hydrophilic group is illustrated in FIG. 20. For the purpose of clarity, this composition can be represented by [L-SMBD-Me-FMBD-H-P-T] plus [L-SMBD-Me-TMBD-H-P]; where H=hydrophobic group: Me=metal ion: FMBD=first metal binding domain; SMBD=second metal binding domain: L=agent or load molecule: P=hydrophilic group: T=targeting group: TMBD=third metal binding domain.

Figure 21:
FIG. 21 depicts a non-limiting diagram of one of the embodiments of the present invention comprising a carrier comprising a hydrophobic group (H; light grey rectangle), a hydrophilic group (P; dashed black wavy line), and a first metal binding domain (FMBD; half-moon dark grey). A metal ion (Me; black oval) is chelated by the FMBD and a second metal binding domain (SMBD; half circle dark grey). The second metal binding domain is linked to or part of the agent (L; dark grey circle with X inside). This component can form a supermolecular structure depicted in FIG. 22.
Figure 22:
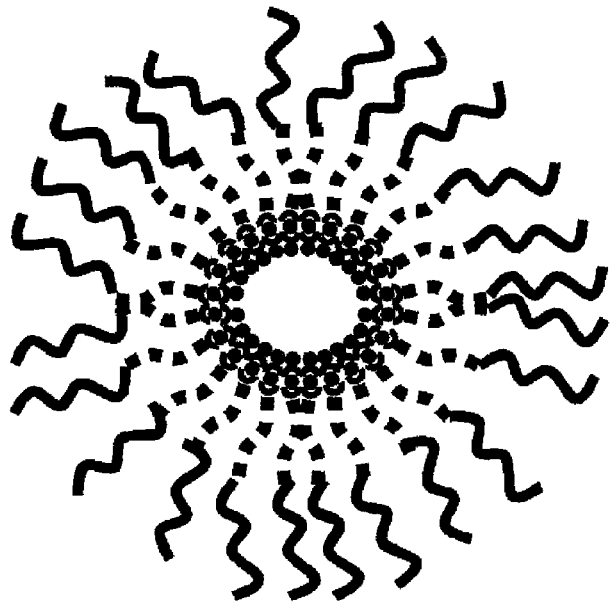
FIG. 22 depicts a non-limiting diagram of a supermolecular structure of one of the embodiments of the present invention comprising a carrier comprising a hydrophobic group (H; light grey rectangle), a hydrophilic group (P; dashed black wavy line), and a first metal binding domain (FMBD; half-moon dark grey). The hydrophilic group P of the carrier has a first end and second end. The first end of the hydrophilic group P of the carrier is linked to the first metal binding domain (FMBD). The second end of the hydrophilic group P of the carrier is linked to the hydrophobic group H of the carrier. A metal ion (Me; black oval) is chelated by the FMBD and a second metal binding domain (SMBD; half circle dark grey). The second metal binding domain is linked to or part of the agent (L; dark grey circle with X inside).
Figure 22:
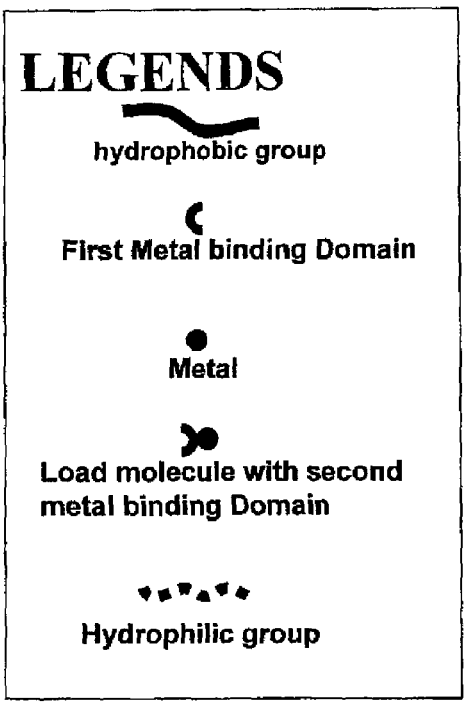

In another embodiment, the composition includes a carrier comprising a hydrophilic group, a hydrophobic group and a FMBD. The FMBD chelates a metal ion. The metal ion is further chelated by a SMBD linked to an agent. The hydrophilic group of the carrier has a first end and second end. The first end of the hydrophilic group of the carrier may be linked to the FMBD, and the second end of the hydrophilic group of the carrier may be linked to a hydrophobic group as illustrated schematically in FIG. 21. One example of a composition comprising (1) a metal ion, a SMBD linked to an agent, and a carrier comprising a hydrophobic group, a hydrophilic group, and a FMBD, is illustrated in FIG. 22. For the purpose of clarity, this composition can be represented by [L-SMBD-Me-FMBD-P-H]; where H=hydrophobic group: Me=metal ion: FMBD=first metal binding domain; SMBD=second metal binding domain: L=agent or load molecule: P=hydrophilic group. As will be recognized, the carrier may further include a targeting group.

Hydrophobic Group

The following descriptions of embodiments are presented to clarify the invention but are not intended to limit the scope of the present invention. The hydrophobic group may have a general formula $[P_vN_wC_xH_yO_z—]$ where v is an integer from 0-3, w is an integer from 0-3, x is an integer from 8-48; y is an integer from 15-95; and z is an integer from 1-13. In a further embodiment, the hydrophobic group comprises an alkyl group. In a further embodiment, the alkyl group has a general formula $[CH_3(CH)_x—]$ where x is 5-35. In a further embodiment, the hydrophobic group is linked to a metal binding domain by an amide, ester, or ether bond. In a further embodiment, the hydrophobic group comprises one or more alkyl group(s) derived from various fatty acids or fatty acids with aromatic group(s). In a further embodiment, the hydrophobic group comprises one or more linear fatty acyl groups with the formula $[CH_3(CH_2)_xCO—]$ where x is an integer from 6-50. In further embodiments, the hydrophobic group comprises phospholipids or derivatives of phospholipids. In further embodiments, the hydrophobic group comprises diacylglecerol or derivatives of diacylglecerol. In a further embodiment, the hydrophobic group comprises a branched or straight chain $C_{5-50}$ alkyl group. In a further embodiment, the hydrophobic group comprises a substituted branched or straight chain $C_{5-50}$ alkyl group. In a further embodiment, the alkyl group has one or more double bonds. In a further embodiment, the alkyl group is an ethyl or propyl group. In a further embodiment, the alkyl group is a butyl, or pentyl group. In a further embodiment, the hydrophobic group comprises hydrophobic polyamino acids. In a further embodiment, the hydrophobic group comprises hydrophobic polyamino acids with molecular weights of from about 100 to about 500,000 Daltons, inclusive. In a further embodiment, the hydrophobic group has a molecular weight ranging from about 50 to about 1000 Daltons. In a further embodiment, the hydrophobic group comprises vitamin D or vitamin E. In a further embodiment, the hydrophobic group comprises phenyl, naphthyl, or cholesterol. In a further embodiment, the hydrophobic group comprises poly-D/L-glycine, poly-D/L-alanine, poly-D/L-valine, poly-D/L-leucine, poly-D/L-Isoleucine, poly-D/L-phenylalanine, poly-D/L-proline, poly-D/L-methionine or their derivatives. In a further embodiment, the hydrophobic group comprises substituted poly-D/L-glycine, poly-D/L-alanine, poly-D/L-valine, poly-D/L-leucine, poly-D/L-Isoleucine, poly-D/L-phenylalanine, poly-D/L-proline, or poly-D/L-methionine.

"Substituted" refers to a group in which one or more hydrogen atoms are each independently replaced with the same or different substituent(s). Typical substituents include —X, —$R^{13}$, —O—, =O, —OR, —$SR^{13}$, —S—, =S, —$NR^{13}R^{13}$, =$NR^{13}$, $CX_3$, —$CF_3$, —CN, —OCN, —SCN, —NO, $NO_2$, =$N_2$, —$N_3$, —S(=O)$_2$O—, —S(=O)$_2$OH, —S(=O)$_2R^{13}$, —OS(=O)$_2$O—, —OS(=O)$_2$OH, —OS(=O)$_2R^{13}$, —P(=O)(O—)$_2$, —P(=O)(OH)(O"), —OP(=O)$_2$(O0, —C(=O)$R^{13}$, —C(=S)$R^{13}$, —C(=O)$OR^{13}$, —C(=O)O$^-$ —C(=S)$OR^{13}$, —$NR^{13}$—C(=O)—N($R^{13}$)$_2$, —$NR^{13}$—C(=S)—N($R^{13}$)$_2$, and —C(=$NR^{13}$)$NR^{13}R^{13}$, wherein each X is independently a halogen; each $R^{13}$ is independently hydrogen, halogen, alkyl, aryl, arylalkyl, arylaryl, arylheteroalkyl, heteroaryl, heteroarylalkyl $NR^{13}R^{14}$, —C(=O)$R^{14}$, and —S(=O)$_2R^{14}$; and each $R^{14}$ is independently hydrogen, alkyl, alkanyl, alkynyl, aryl, arylalkyl, arylheteralkyl, arylaryl, heteroaryl or heteroarylalkyl. Aryl containing substituents, whether or not having one or more sustitutions, may be attached in a para (p-), meta (m-) or ortho (o-) conformation, or any combination thereof.

Metal Binding Domain

In general, the metal binding domains used in the present invention contain a Lewis base fragment that is contemplated to encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in the metal binding domain include: amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, bisphosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable metal binding domains include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in the metal binding domains include the following chemical moieties: amines, particularly alkylamines and arylamines, including methylamine, diphenylamine, trimethylamine, triethylamine, N,N-dimethylaniline, methyldiphenylaniline, pyridine, aniline, morpholine, N-methyUnorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolaminejN-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in the metal binding domains include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligand fragments for use in the metal binding domains include structural moieties that are bidentate ligands, including diimines, pyridylimines, diamines, iminoamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in the metal binding domains include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or may be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

Further examples of chelating groups which act as the metal binding domain and can be chemically linked to the hydrophobic group or hydrophilic group include 1,4,7,10- tetraazacyclododecane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane, 1,4,7-triazacyclonane-N,N',N''-triacetic acid; and 1,4,8,11-tetraazacyclotetra-decane-N,N',N'',N'''-tetraacetic acid; diethylenetriamine-pentaacetic acid (DTPA); triethylenetetraamine-hexaacetic acid; ethylenediamine-tetraacetic acid (EDTA); EGTA; 1,2-diaminocyclohexane-N,N,N',N'-tetraacetic acid but preferably N-(hydroxyethyl)ethylenediaminetriacetic acid; nitrilotriacetic acid (NTA); and ethylene-bis(oxyethylene-nitrilo)tetraacetic acid, histidine, cysteine, oligoaspartic acid, oligoglutamic acid, S-acetyl mercaptoacetate and meractoacetyltriglycine.

In a further embodiment, the present invention relates to the above described composition wherein the metal binding domain comprises a nitrogen containing poly carboxylic acid. In a further embodiment, the metal binding domain comprises one or more of the following moieties: N-(hydroxy-ethyl)ethylenediaminetriacetic acid; nitrilotriacetic acid (NTA); ethylene-bis(oxyethylene-nitrilo)tetraacetic acid; 1,4,7,10-tetraazacyclodo-decane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; bisphosphonate; or metal binding polypeptide.

In one embodiment, the metal binding domain is a polypeptide. For example, the polypeptide may have the formula $(A_xH_y)_p$ where A is any amino acid, H is histidine, x is an integer from 0-6; y is an integer from 1-6; and p is an integer from 1-6.

In one embodiment, the metal binding domain is a bisphosphonate derivative.

A metal ion may be chelated by more than one metal binding domain. For example, a metal ion may be chelated by a first metal binding domain and a second metal binding domain. The first metal binding domain and the second metal binding domain may each be individually capable of chelating the metal ion. Alternatively or additionally, the first metal binding domain and the second metal binding domain may be capable of chelating the metal ion simultaneously.

Metal Ion

The present invention contemplates the use of a variety of different metal ions. The metal ion may be selected from those that have usually two, three, four, five, six, seven or more coordination sites. A non-limiting list of metal ions for which the present invention may be employed (including exemplary and non-limiting oxidation states for them) includes $Co^{3+}$, $Cr^{3+}$ $Hg^{2+}$, $Pd^{2+}$ $Pt^{2+}$ $Pd^{4+}$ $Pt^{4+}$ $Rh^{3+}$ $Ir^{3+}$ $RU^{3+}$ $Co^{2+}$ $Ni^{2+}$ $Cu^{2+}$ $Zn^{2+}$, $Cd^{2+}$ $Pb^{2+}$, $Mn^{2+}$, $Fe^{3+}$, $Fe^{2+}$, Tc, $Au^{3+}$, $Au^+$, $Ag^+$, $Cu^+$, $MoO_2^{2+}$, $Ti^{3+}$, $Ti^{4+}$, $CH_3Hg^+$, and $Y^{+3}$. In another embodiment, the non-limiting list of metal ions for which the present invention may be employed includes $Zn^{2+}$, $Ni^{2+}$, $Co^{2+}$, $Fe^{2+}$, $Mn^{2+}$, and $Cu^{2+}$. The metal ion contained in the metal bridge between the hydrophobic group or hydrophilic group and the agent may have a therapeutic use itself, but it cannot serve as the agent.

In a further embodiment, the present invention relates to the above described composition wherein the metal ion is a transition metal ion. In a further embodiment, the metal ion is one or more of the following: $Zn^{2+}$, $Ni^{2+}$, $Co^{2+}$, $Fe^{2+}$, $Mn^{2+}$, or $Cu^{2+}$.

Hydrophilic Group

The term "hydrophilic group" refers to any hydrophilic moiety. In certain embodiments, the hydrophilic group is linear or a branched polymer or copolymer. Non-limiting examples of hydrophilic groups are: poly(ethylene glycol); alkoxy poly(ethyleneglycol); methoxy poly(ethylene glycol); dicarboxylic acid esterified poly(ethylene glycol) monoester; poly(ethylene glycol)-diacid; copolymer of poly(ethylene glycol); poly(ethylene glycol) monoamine; methoxy poly(ethylene glycol) monoamine; methoxy poly(ethylene glycol) hydrazide; methoxy poly(ethylene glycol) imidazolide; blockcopolymer of poly(ethylene glycol); polylactide-glycolide co-polymer; polysaccharide; oligosaccharides; polyamidoamine; and polyethyleneimine.

In some embodiments, the hydrophilic group is capable of providing protection to the supermolecular structure or agents associated with the supermolecular structure or both. In some instances, the hydrophilic group is capable of protecting the supermolecular structure and/or agent through sterics (i.e., steric protection). The hydrophilic group may also protect the supermolecular structure and/or agent by reducing or preventing degradation of the supermolecular structure and/or agent. The hydrophilic group may protect the supermolecular structure and/or agent by reducing or preventing chemical reactions involving the supermolecular structure and/or agent. In some embodiments, the hydrophilic group may reduce the recognition of the supermolecular structure and/or agent by the patient or subject (i.e., the patient's or subject's immune system). For example, the hydrophilic group may reduce the recognition of the supermolecular structure and/or agent by the reticuloendothelial system (i.e., sequestration by various cells) or by opsonization (i.e., antibody mediated complement formation and elimination by macrophages). The hydrophilic group may provide an increased half life to the supermolecular structure and/or agent.

Targeting Group

The term "targeting group" refers to any molecular structure which assists the construct or supermolecular structure in localizing to a particular target area, entering a target cell(s), and/or binding to a target receptor. Non-limiting examples of targeting groups are: an antibody, cell surface receptor ligands, cell surface binding saccharide ligands, extracellular matrix ligands, cytosolic receptor ligands, growth factors, cytokines, incretin, hormones, quasi substrates of cell surface enzymes, and lectin. An antibody includes, for example, a fragment of an antibody, chimeric antibodies, humanized antibodies, polyclonal antibodies, and monoclonal antibodies. A cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. An extracellular matrix ligand includes, for example, an extracellular matrix binding peptide, an extracellular matrix binding glycopeptide, an extracellular matrix binding protein, an extracellular matrix binding glycoprotein, an extracellular matrix binding organic compound, and an extracellular matrix binding drug. A cytosolic receptor ligand includes, for example, a cytosolic receptor binding peptide, a cytosolic receptor binding glycopeptide, a cytosolic receptor binding protein, a cytosolic receptor binding glycoprotein, a cytosolic receptor binding organic compound, and a cytosolic receptor binding drug.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida* sp.). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

Agent

The term "agent" as used herein refers to any therapeutic agent or diagnostic agent.

The term "therapeutic agent" as used herein refers to any moiety that is a biologically, physiologically, or pharmacologically active substance that acts locally or systemically in a subject. In some embodiments, the therapeutic agent is a metal binding chemical moiety. Some examples of therapeutic agents are described in well-known literature references such as the Merck Index, the Merck manual of diagnosis and therapy, the Physicians Desk Reference, and The Pharmacological Basis of Therapeutics. They include in the list metal binding proteins, peptides, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a metal binding therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynernicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), siRNA, peptides, proteins, antibodies, photodynamic agents (e.g., rhodamine 123), radionuclides (e.g., 1-131, Re-186, Re-188, Y-90, Bi-212, At-211, Sr-89, Ho-166, Sm-153, Cu-67 and Cu-64), toxins (e.g., ricin), and transcription-based Pharmaceuticals.

The term "diagnostic" or "diagnostic agent" is any moiety that may be used for diagnosis. For example, diagnostic agents include imaging agents containing radioisotopes such as indium or technetium; contrasting agents containing iodine, technetium, or gadolinium; enzymes such as horse radish peroxidase, GFP, alkaline phosphatase, or beta-galactosidase; fluorescent substances such as europium derivatives; luminescent substances such as N-methylacrydium derivatives or the like.

In a further embodiment, the present invention relates to the above described compositions wherein the agent is one of the following: a metal binding diagnostic protein imaging agent, a metal binding diagnostic enzyme imaging agent, a metal binding diagnostic fluorophore imaging agent, a metal binding diagnostic nuclear-imaging agent, a metal binding diagnostic paramagnetic imaging agent, a metal binding peptide therapeutic agent, a metal binding protein therapeutic agent, a metal binding peptide therapeutic agent, a metal binding organic compound therapeutic agent, a metal binding peptidomimetic therapeutic agent, a metal binding deoxyribonucleic acid therapeutic agent, a metal binding ribonucleic acid therapeutic agent, a metal binding oligonucleotide therapeutic agent, a metal binding nucleic acid therapeutic agent, a metal binding oligosaccharide therapeutic agent, a metal binding antibody therapeutic agent or a metal binding proteoglycan therapeutic agent. In a further embodiment, the present invention relates to the above described compositions wherein more than one type of agent forms a coordinate bond with the metal binding domain linked to a hydrophobic group or hydrophilic group.

It understood that the term "diagnosis" as it refers to the use of the composition indicates that the composition will be used as a contrast agent to obtain an image of the patient's body to determine the region where the composition of the present invention accumulates. This information will have diagnostic value in a patient with various diseases since most diseases cause vascular changes that can be imaged or diagnosed by the compositions of the present invention. Non-limiting examples of these diseases include cancer, inflammation, arthritis, stroke victim, and other vascular abnormalities. In addition, compositions of the present invention can be made to localize and accumulate at site(s) where there are specific antigens, cell markers, or molecules in the body which can help in the diagnosis to determine the presence and localization of specific molecules or antigens in the body. This approach is known to those with ordinary skill in the art.

Another example of a diagnostic agent is radionuclides, which may be detected using positron mission tomography (PET) or single photon emission computed tomography (SPECT) imaging or other methods known to one of skill in the art. In one embodiment, the composition of the present invention comprises one of the following radionuclides: $^{131}$I, $^{125}$I, $^{123}$I, $^{99m}$Tc, $^{18}$F, $^{68}$Ga, $^{67}$Ga, $^{72}$As, $^{89}$Zr, $^{64}$Cu, $^{62}$Cu, $^{111}$In, $^{203}$Pb, $^{198}$Hg, $^{11}$C, $^{97}$Ru, and $^{201}$Tl or a paramagnetic contrast agent, such as gadolinium, cobalt, nickel, manganese and iron. Such moieties may be chelated to their own metal binding domain which in turn could be coordinated to the metal ion found in the bridge to the hydrophobic group or hydrophilic group.

Non-limiting examples of agents include insulin, growth factors, hormones, cytokines, growth hormone (GH, somatropin), nerve growth factor (NGF), lysostaphin, GLP-1, brain-derived neurotrophic factor (BDNF), enzymes, endostatin, angiostatin, trombospondin, urokinase, interferon, blood clotting factors (VII, VIII), and any molecule able to bind metal ions.

Amphipathic Constituents

An amphipathic constituent contains at least one hydrophobic group (e.g., but not limited to: alkyl, aromatic alkyl, hydrophobic polyamino acids) and at least one hydrophilic group (e.g., but not limited to: metal ions, charged metal, binding domains, charged agents).

Supermolecular Structure

Supermolecular structures include vesicular structures such as microemulsions, liposomes, and micellar and reverse micellar structures. Liposomes can contain an aqueous volume that is entirely enclosed by a membrane composed of lipid molecules (usually phospholipids). Micelles and reverse micelles are microscopic vesicles that contain amphipathic constituents but do not contain an aqueous volume that is entirely enclosed by a membrane. In micelles the hydrophilic part of the amphipathic compound is on the outside (on the surface of the vesicle) whereas in reverse micelles the hydrophobic part of the amphipathic compound is on the outside. The reverse micelles thus contain a polar core that can solubilize both water and macromolecules within the inverse micelle. As the volume of the core aqueous pool increases the aqueous environment begins to match the physical and chemical characteristics of bulk water. The resulting inverse micelle can be referred to as a microemulsion of water in oil.

In water, when a sufficient concentration of the components that make up a micelle are present, the components spontaneously aggregate into thermodynamically stable supermolecular structures. The supermolecular structure particles may assume a microspheroidal shape and possess, in essence, a double layer. The core "layer" may form by virtue of the hydrophobic interactions between, for example, hydrophobic polyesters or alkyl groups. Similarly, the surface "layer" may form by virtue of the corresponding hydrophilic interactions of a, for example, hydrophilic polycation or polyanion with water. A net charge will exist around the surface of the micelle, since the hydrophilic segment of the first component is charged. Alternatively, the surface "layer" of the supermolecular structure particles may have a hydrophilic portion that is not charged but can attract water molecules, for example, hydrophilic poly ether such as polyethylene glycol.

Functional compounds having metal binding properties can be easily introduced to the micelle by: (1) creating a third copolymer component that bears the functional group and (2) coupling the third copolymer to the surface of a pre-assembled polymeric micelle. Alternatively, a metal binding domain-bearing component can be incorporated into a component of a micelle prior to micelle formation. If so, then it may be preferable to use a hydrophilic component wherein the metal binding domain resides so that it is exposed in the micelle surface layer in a water environment or inside the reversed micelle in a hydrophobic environment or solvent. It is an advantage of the present invention that the kind and content of the functional group can be easily changed without limitation.

Micelles according to the present invention may comprise biodegradable, biocompatible components, resulting in non-immunogenicity and non-toxicity. In one aspect components disclosed herein degrade into non-toxic, small molecules subject to renal excretion and are inert during the required period of treatment. Degradation may occur via simple hydrolytic and/or enzymatic reaction. Degradation through simple hydrolysis may be predominant when the components comprise ester bonds. Enzymatic degradation may become significant in the presence of certain organelles such as lysosomes. The degradation period can be varied from days to months by using components of different kinds and molecular weights. Accordingly, the advantageous components and structure of micelles according to the present invention can be appreciated regarding reduced cytotoxicity. For additional examples of micelles, reverse micelles, liposomes, and microspheres suitable for the present invention see U.S. Pat. Nos. 6,338,859, 5,631,018; 6,162,462; 6,475,779; 6,521,211; and 6,443,898, which are herein incorporated by reference.

Emulsions as the composition in the present invention relate to emulsions of an aqueous or an aqueous-organic continuous phase and an organic discontinuous phase, the latter containing an organic solvent which is not miscible with water. Hydrogels are similar and refer to a type of gel in which the disperse phase has combined with water to produce a semisolid material. The emulsions and hydrogels used in the present invention may contain organic compounds from the group of the reaction products of alkylene oxides with compounds capable of being alkylated, such as, for example, fatty alcohols, fatty amines, fatty acids, phenols, alkylphenols, carboximides and resinic acids, preferably balsamic resin and/or abietic acid. A supermolecular structure in the present invention may be mixed with a gelating material or a material that increases viscosity to form hydrogel. Hydrogel formulations are useful for topical application of agents.

Organic solvents which are not miscible with water include, for example, aliphatic, cycloaliphatic or aromatic hydrocarbons or the acetate-type solvents. Suitable as organic solvents are, preferably, natural, fully- or semisynthetic compounds and, if appropriate, mixtures of these solvents which are fully miscible or soluble with the other compounds of the emulsion in the temperature range of from 20 to 130° C. In one embodiment, suitable solvents are those from the group of the aliphatic, cycloaliphatic or aromatic hydrocarbons which are liquid at room temperature, including oils, such as, for example, mineral oils; paraffins, isoparaffins, fully-synthetic oils such as silicon oils, semi-synthetic oils based on, for example, glycerides of unsaturated fatty acids of medium chain length, essential oils, esters of natural or synthetic, saturated or unsaturated fatty acids, for example $C_8$-$C_{22}$-fatty acids, $C_8$-$C_{18}$-fatty acids, especially preferably methyl esters of rapeseed oil or 2-ethylhexyl laurate, alkylated aromatics and their mixtures, alkylated alcohols, in particular fatty alcohols, linear, primary alcohols obtained by hydroformylation, terpene hydrocarbons and naphtene-type oils, such as, for example, Enerthene. Further organic solvents include those from the group of the acetate-type solvents such as, for example, 1,2-propanediol diacetate, 3-methyl-3-methoxybutyl acetate, ethyl acetate and the like. The solvents can be employed individually or as mixtures with each other.

The continuous aqueous or aqueous-organic phase of the active-agent-containing emulsions or microemulsions according to the present invention contain water, an organic solvent that is soluble or miscible in water, and may also contain at least one natural or synthetic surface-agent which has a solubility of >10 g/l, in particular >100 g/l in water (d) at 20° C., and, if appropriate, further adjuvants. Organic solvents which are soluble or miscible in water have a solubility in water of >5.0 g/l at 20° C., in particular >15 g/l.

Examples of suitable organic solvents are aliphatic $C_1$-$C_4$-alcohols such as methanol, ethanol, isopropanol, n-propanol, n-butanol, isobutanol or tert-butanol, aliphatic ketones such as acetone, methyl ethyl ketone, methyl isobutyl ketone or diacetone alcohol, polyols, such as ethylene glycol, propylene glycol, butylene glycol, 1,4-butanediol, 1,5-pentanediol, 1,6-hexanediol, diethylene glycol, triethylene glycol, trimethylolpropane, polyethylene glycol or polypropylene glycol with a mean gram-molecular weight of 100 to 4000 g/mol or 200 to 1500 g/mol, or glycerol, monohydroxyethers, such as monohydroxyalkyl ethers or mono-$C_1$-$C_4$-alkyl glycol ethers such as ethylene glycol monoethyl ether, ethylene glycol monomethyl ether, diethylene glycol monomethyl ether or diethylene glycolmonoethyl ether, diethylene glycol monobutyl ether, dipropylene glycol monoethyl ether, thiodiglycol, triethylene glycol monomethyl ether or triethylene glycol monoethyl ether, furthermore 2-pyrrolidone, N-methyl-2-pyrrolidone, N-ethyl-pyrrolidone, N-vinylpyrrotidone, 1,3-dimethylimidazolidone, dimethylacetamide and dimethyl formamide.

The amount of the solvents employed in the aqueous continuous phase is in general less than 60% by weight or less than 40% by weight, based on the continuous phase.

Surface-agents are understood as meaning emulsifiers, wetters, dispersants, antifoams or solubilizers which are soluble or fully soluble, in the aqueous phase. In particular, they can be nonionic, anionic, cationic or amphoteric or of monomeric, oligomeric or polymeric nature. The choice of the surface-agents is not limited in accordance with the present invention and must be matched with the discontinuous phase to be stabilized with regard to the desired type of emulsion (for example miniemulsion or microemulsion) and the stability of the emulsion, in particular the sedimentation and/or creaming of the disperse phase.

In another embodiment, the continuous aqueous phase can also contain, in addition to the abovementioned surface-agents, water-soluble block or block copolymers; these block or block copolymers include water-soluble block and block copolymers based on ethylene oxide and/or propylene oxide and/or water-soluble block and block copolymers of ethylene oxide and/or propylene oxide on bifunctional amines. Block copolymers based on polystyrene and polyalkylene oxide, poly(meth)acrylates and polyalkylene oxide and also poly(meth)acrylates and poly(meth)acrylic acids are also suitable.

In addition, the continuous aqueous phase can also contain further customary adjuvants such as, for example, water-soluble welters, antifoams and/or preservatives.

Emulsion types of the present invention include macroemulsion which contains droplets >2 μm (microscopic); miniemulsion which has a droplet diameter 0.1 to 2 μm, turbid; and microemulsion which has a droplet diameter <0.1 μm, transparent. For additional examples of emulsions and hydrogels suitable for the present invention see U.S. Pat. Nos. 6,458,373 and 6,124,273 which are incorporated herein by reference.

Creating Links Between Hydrophobic Groups, Metal Binding Domains, Hydrophilic Groups and Targeting Groups A hydrophobic group of the invention may be linked to a metal binding domain. A hydrophobic group of the invention may also be linked to a hydrophilic group of the invention. Likewise, a hydrophilic group of the invention may be linked to a metal binding domain and/or a targeting group. In some embodiments, the groups and/or domains are linked by a chemical linkage. For example, the chemical linkage may be a covalent linkage. The preferred type of chemical link to use in attaching the hydrophobic groups, metal binding domains, hydrophilic groups, and targeting groups to each other can be ether, amide, ester, or disulfide bonds. Mixtures of these chemical bonds can also be used for ease of synthesis and to achieve the desired properties such as biodegradability.

The chemical link may comprise modified acyl groups at one end of the hydrophobic group. A modified acyl group can be the amide linkage of a hydrophobic functional group to the amino group of metal binding domains or hydrophilic groups. These modified acyl groups may comprise an alkyl acyl derived from fatty acids, or aromatic alkyl acyl derived from aromatic alkyl acids which has a general formula $[C_xH_yO_z]$ where x is 2-36; y is 3-71; z is 1-4. In most cases z=1, which is the minimum required for an amide bond with the amino group. The starting molecules however may have z greater than 1 prior to amide bond formation. Alternatively, modified acyl groups comprise hydrophobic polyaminoacids such as poly-L-glycine, poly-L-alanine, poly-L-valine, poly-L-leucine, poly-L-isoleucine, poly-L-phenylanine, poly-D-glycine, poly-D-alanine, poly-D-valine, poly-D-leucine, poly-D-isoleucine, poly-D-phenylanine, poly-D/L-glycine, poly-D/L-alanine, poly-D/L-valine, poly-D/L-leucine, poly-D/L-isoleucine, poly-D/L-phenylanine, poly-D/L-proline, and poly-D/L-methionine. One end of the polyamino acid may be capped to neutralize the charge such as by methylation, acetylation, or amidation and the other end may be linked to a metal binding domain or hydrophilic group.

In another embodiment, the hydrophobic functional groups may comprise two ended hydrophobic alkyl groups, which have a general formula [—OC(CH$_2$)$_x$CO—] or [-OC(CH$_2$)$_x$CN—] where x is 2-36, and linked to a hydrophilic group at one end and a metal binding domain in the other end.

The hydrophobic functional group may be linked to a protective hydrophotib group by a chemical linkage, including a covalent chemical linkage. The chemical bond linking the former [—OC(CH$_2$)$_x$CO—] will be amide or ester and the latter [—OC(CH$_2$)$_x$CN—] will be amide or ester at the first end and amide at the second end. In another embodiment the hydrophobic group is a hydrophobic polyamino acid or derivatives thereof such as but not limited to poly-L-glycine, poly-L-alanine, poly-L-valine, poly-L-leucine, poly-L-isoleucine, poly-L-phenylanine, poly-D-glycine, poly-D-alanine, poly D valine, poly-D-leucine, poly-D-isoleucine; poly-D-phenylanine, poly-D/L-glycine, poly-D/L-alanine, poly-D/L-valine, poly-D/L-leucine, poly-D/L-isoleucine, poly-D/L-phenylanine, poly-D/L-proline, and poly-D/L-methionine. The carboxy terminal or the amino terminal may be linked by an amide bond to a metal binding domain, a hydrophilic group, or a moiety that removes the charge to make the terminal hydrophobic. This can be achieved by methylation, acetylation, amidation, and other derivatization well known to those with ordinary skill in the art.

Figure 23:
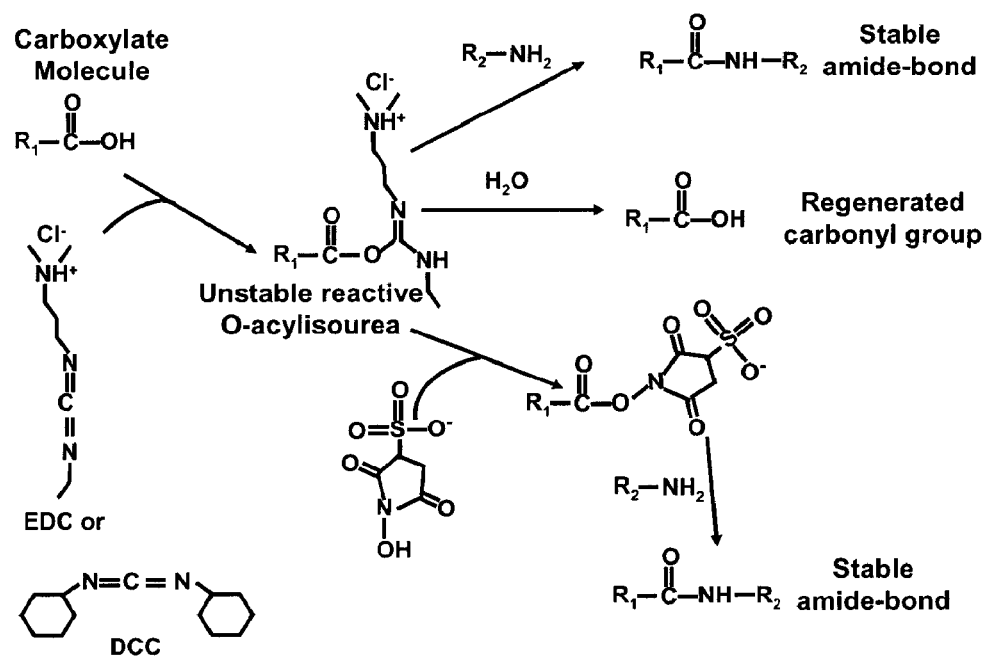
FIG. 23 depicts a non-limiting diagram of various chemical reactions for making amide bonds that are useful in making the composition of the invention; $R_1$ can be alkyl-carboxyl or aromatic-alkyl carboxyl and $R_2$ can be aminated metal binding domain, or aminated protective hydrophilic chain; or $R_1$ can be carboxylated protective hydrophilic chain and $R_2$ can be aminated metal binding domain, aminated targeting molecule, or can be alkyl-amino or aromatic-alkyl amino. EDC is a water soluble version of DCC; both can be used to carry out the reactions.
Figure 24:
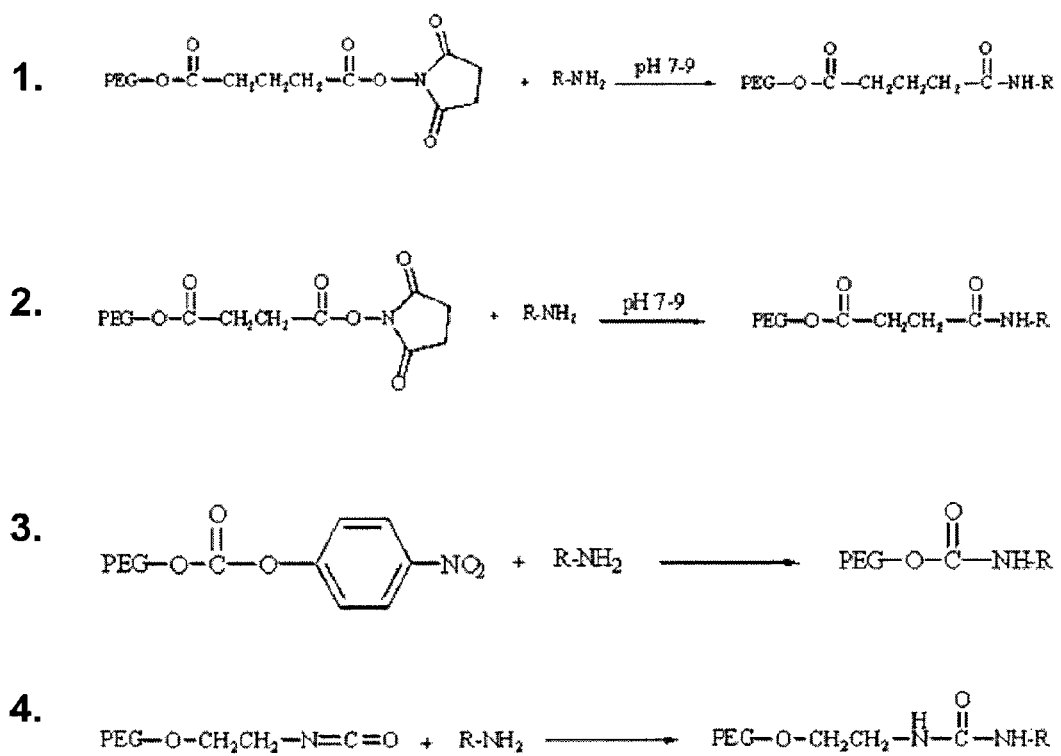
FIG. 24 depicts some of the chemical reactions that may be used to add hydrophilic groups (P), analogs or derivatives thereof, to amino group containing alkyl chains, amino group containing metal binding domains, or amino groups containing targeting molecules.
Figure 25:
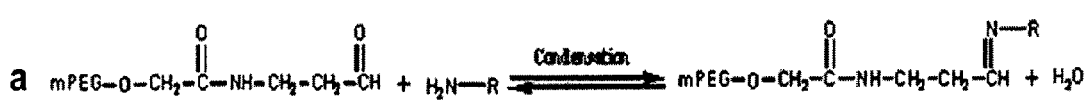
FIG. 25 depicts some of the chemical reactions that may be used to add aldehyde PEG (a hydrophilic group P) derivatives to aminated metal binding domains, aminated targeting molecules, aminated alkyl-groups or aminated aromatic-alkyls. These are two step condensation-reduction reactions.
Figure 25:
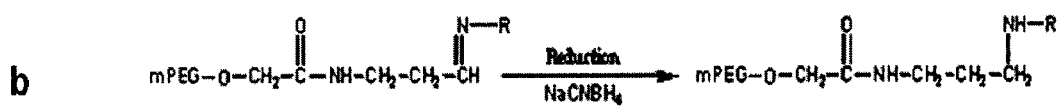
Figure 25:
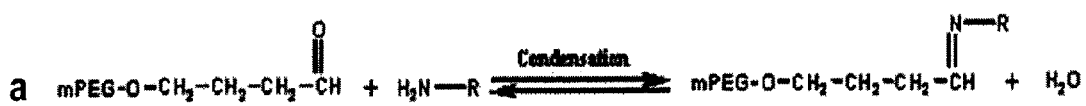
Figure 25:
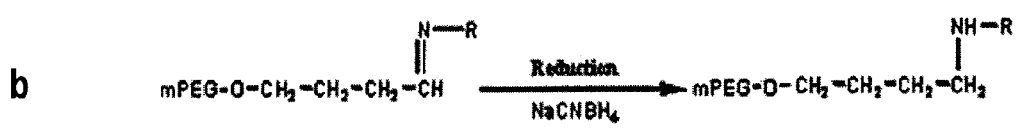
Figure 25:
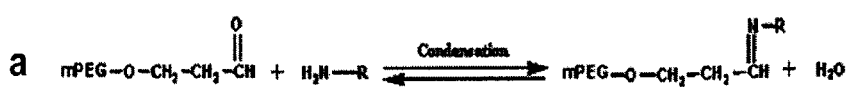
Figure 25:
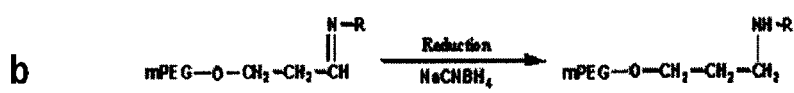
Figure 26:
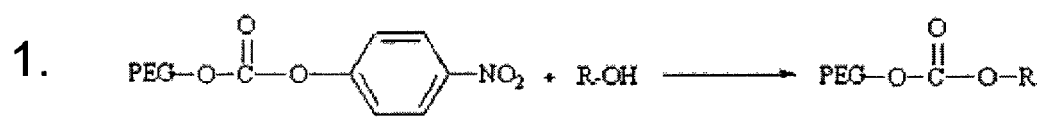
FIG. 26 depicts some of the chemical reactions that may be used to add PEG protective groups, analogs or derivatives thereof, to hydroxyl containing metal binding domains, hydroxyl containing targeting molecules, hydroxyl containing alkyl-groups or hydroxyl containing aromatic-alkyls.
Figure 26:
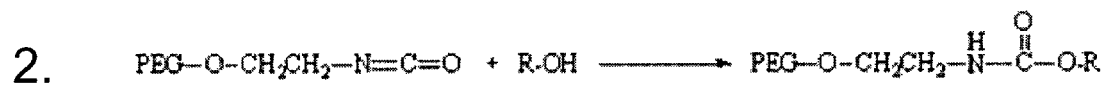
Figure 26:
Figure 27:
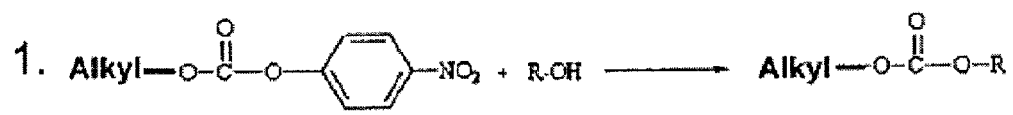
FIG. 27 depicts some of the chemical reactions that may be used to add alkyl hydrophobic groups to hydroxyl containing metal binding domains, hydroxyl containing targeting molecules, hydroxyl containing alkyl-groups or hydroxyl containing aromatic-alkyls.
Figure 27:
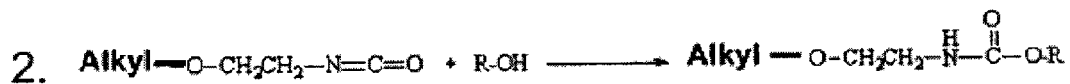
Figure 27:
Figure 28:
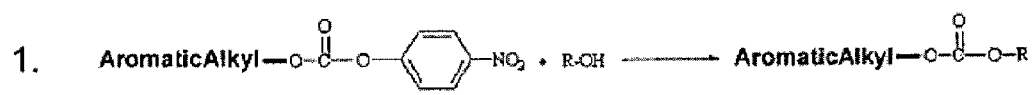
FIG. 28 depicts some of the chemical reactions that may be used to add aromatic alkyl hydrophobic groups to hydroxyl containing metal binding domains, hydroxyl containing targeting molecules, hydroxyl containing alkyl-groups or hydroxyl containing aromatic-alkyls.
Figure 28:
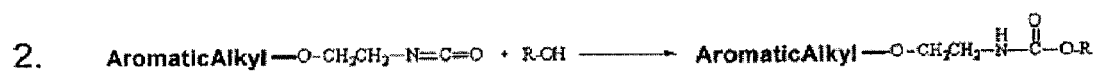
Figure 28:

A hydrophobic group can be attached to an amino group-containing metal binding domain or an amino group-containing hydrophilic group by an amide bond formation. As an example that is not intended to limit the scope of this invention, the carboxyl containing hydrophobic molecule can be attached to the amino group of the metal binding domain or amino group of a hydrophilic group using a carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of the coupling reaction, the activated carboxyl group (O-acylisourea-intermediate) can optionally be stabilized by forming N-hydroxysuccinimide ester using N-hydroxysuccinimide. This relatively stable intermediate can react with the amino group of a metal binding domain or hydrophilic group to form amino-acyl bond or amide bond (see FIG. 23). Similar reactions can also be used to attach a carboxyl containing targeting group to an amino group containing hydrophilic group with the resulting formation of an amino-acyl bond or an amide bond.

Another way to attach a hydrophobic group is to chemically react an amino group of a metal binding domain or an amino group of a hydrophilic group with a hydrophobic fatty acid anhydride. For example, reaction of the amino group of a metal binding domain or the amino group of a hydrophilic group with palmitic acid anhydride forms a component of the composition of the present invention. Any fatty acid anhydride may be used in this fashion. Similar reactions can also be used to attach an anhydride containing targeting group to an amino group containing a hydrophilic group with the resulting formation of an amino-acyl bond or an amide bond.

In some embodiments of the invention, a hydrophobic group is attached to a metal binding domain or a hydrophilic group with carboxyl groups. The attachment can be done by amide bond formation. As an example that is not intended to limit the scope of this invention, the carboxyl group of the metal binding domain or the hydrophilic group can be activated to react with amino functional groups of the amino group containing hydrophobic groups. The activation can be accomplished using carbodiimide containing reagents such a 1-ethyl-3-(3-dimethylaminopropyl)-carbodiimide or dicyclohexylcarbodiimide. A carbodiimide reagent contains a functional group consisting of the formula N=C=N. During the process of activation, the carboxyl group forms a O-acylisourea-intermediate that can optionally be stabilized by N-hydroxysuccinimide to form N-hydroxysuccinimide ester. This relatively stable intermediate can react with the amino group of hydrophobic groups. If the hydrophobic group or molecule does not have an amino group, the amino group can be introduced to this molecule very easily and the chemistry is well known to those with skill in the art.

A hydrophobic group may also be attached to a hydroxyl group containing a metal binding domain or a hydroxyl group containing a hydrophilic group. The modification of a hydroxyl group can be facilitated by synthesis of an acyl halide of fatty acids, carboxyl aromatic hydrocarbons, or dicarboxylic alkyl. Synthesis of acyl halides can be done by reaction of the carboxylic acid moiety with dichlorosulfoxide ($SOCl_2$) or other reagents known to those skilled in the art. The resulting acyl halides are reactive to alcohol functional groups present in hydroxyl group containing metal binding domains or hydroxyl group containing hydrophilic groups. The reaction will result in an ester bond formation attaching the hydrophobic groups or molecules to the metal binding domain or hydrophilic group. Similar reactions can also be use to attach a hydroxyl group containing hydrophilic group to a targeting molecule containing a carboxyl group which was converted to acyl halide.

Another way to attach a hydrophobic group through forming an ester bond with a hydroxyl containing hydrophilic group or a hydroxyl containing metal binding domain is to react the hydroxy groups with a fatty acid anhydride. For example, reaction of a hydroxy group, in the hydroxyl containing hydrophilic group or hydroxyl containing metal binding domain, with palmitic acid anhydride forms an ester linkage with a long chain hydrophobic group comprising 16 carbons. Any fatty acid anhydride may be used in this fashion. Similar reactions can also be used to attach a hydroxyl group containing hydrophilic group to a targeting molecule containing anhydride.

Components of the compositions may be synthesized as described above and illustrated in FIGS. 23-28 and the reactions are very well known to those with ordinary skill in the art. The steps of synthesis are also demonstrated by exemplification in U.S. Patent Application Publication No. 2003/0224974 which is incorporated by reference into the present application.

Sustained Release

If a subject composition is formulated with an agent, release of such an agent for a sustained or extended period as compared to the release from an isotonic saline solution generally results. Such release profile may result in prolonged delivery (over, about 1 to about 4,000 hours, or alternatively over from about 4 to about 1500 hours) of effective amounts (e.g., about 0.00001 mg/kg/hour to about 10 mg/kg/hour) of the agent or any other material associated with the composition of the present invention.

A variety of factors may affect the rate of dissociation of an agent of the subject invention. Some of the factors include: the selection of various coordinating groups on the metal ion, whether the agents are inside or on the surface of the supermolecular structure, and the type of linkages in the components in the carrier which relates to how fast cells or enzymes can degrade the carrier and release the agents.

To illustrate further, a wide range of dissociation rates may be obtained by adjusting the hydrophobicities of the backbones or side chains of the components of the supermolecular structure while still maintaining sufficient biodegradability. Such a result may be achieved by varying the various functional groups of the components. For example, the combination of a hydrophobic group and a hydrophilic metal ion containing bridge between the carrier and agent produces heterogeneous release because dissociation is encouraged whereas water penetration is resisted. In addition the formation of supermolecular structures with the internal portion containing bound agent and the external surface containing bound agent will have two release profiles: one, for the agent being released from the surface; and two, for the agent being released from the internal cavity as the supermolecular structures degrades. It is understood that not all the supermolecular carriers will degrade at once but rather will degrade with specific half-lives, depending on the composition and chemical bonds that were used to make each of the components. This will result in sustained release of the agent in the internal portion of the structure, the rate of which is proportional to the rate of degradation of the supermolecular structure. It is also understood that the agent in the surface is protected from rapid degradation in biological fluid by the hydrophilic group on the surface causing steric hindrance to enzymes and cells. In certain embodiments, when formulated in a certain manner, the release rate of the agent from the supermolecular molecule of the present invention may present as mono- or bi-phasic. Release of any material incorporated into the supermolecular structure, which may be provided as a microsphere, may be characterized in certain instances by an initial increased release rate, which may release from about 5 to about 50% or more of the agent or alternatively about 10, 15, 20, 25, 30 or 40%, followed by a release rate of lesser magnitude.

One protocol generally accepted in the field that may be used to determine the release rate of any agent or other material attached to the exterior surface of the carrier through a metal ion bridge of the present invention involves dissociation of any such agent or other material in a 0.1 M PBS solution (pH 7.4) at 37° C., an assay known in the art. For purposes of the present invention, the term "PBS protocol" is used herein to refer to such protocol. For an agent in the interior portion of the supermolecular structure, the assay is ideally performed in cell culture where the supermolecular structure may be metabolized by cells at a specific rate and the agent made available to cells at the same rate. More ideally, the release rate determination should be performed in vivo or in experimental animals. In certain instances, the release rates of different supermolecular structures of the present invention may be compared by subjecting them to such a protocol. In certain instances, it may be necessary to process the supermolecular structure in the same fashion to allow direct and relatively accurate comparisons of different systems to be made. Such comparisons may indicate that any one supermolecular structure releases the agent at a rate from about 2 or less to about 1000 or more times faster than another polymeric system. Alternatively, a comparison may reveal a rate difference of about 3, 5, 7, 10, 25, 50, 100, 250, 500 or 750. Even higher rate differences are contemplated by the present invention and release rate protocols.

The release rate of the agent may also be characterized by the amount of such material released per day per mg of carrier. For example, in certain embodiments, when the carrier is a polymer, the release rate may vary from about 1 ng or less of agent per day per mg of polymeric system to about 5000 or more ng/day/mg. Alternatively, the release rate may be about 10, 25, 50, 75, 100, 125, 150, 175, 200, 250, 300, 350, 400, 450, 500, 600, 700, 800 or 900 ng/day/mg. In still other embodiments, the release rate of the agent may be 10,000 ng/day/mg or even higher. In certain instances, agents characterized by such release rate protocols may include therapeutic agents, or diagnostic imaging agents.

In another aspect, the rate of release of an agent from any carrier of the present invention may be presented as the half-life of such material in such matrix.

In addition to the embodiment involving protocols for in vitro determination of release rates, in vivo protocols, whereby in certain instances release rates of agents from the carrier may be determined in vivo, are also contemplated by the present invention. Other assays useful for determining the release of agents from the carriers of the present invention may be envisioned.

Dosages

The dosage of any compound of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention contemplates mixtures of more than one subject compound, as well as other therapeutic agents.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular compound of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Formulation

The compounds of the present invention may be administered by various means, depending on their intended use, as is well known in the art. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eye-drops or eye-ointments. These formulations may be prepared by conventional means, and, if desired, the compounds may be mixed with any conventional additive, such as an excipient, a binder, a disintegrating material, a lubricant, a corrigent, a solubilizing material a suspension aid, an emulsifying material or a coating material.

In formulations of the subject invention, wetting materials, emulsifiers and lubricants, such as sodium lauryl sulfate and magnesium stearate, as well as coloring materials, release materials, coating materials, sweetening, flavoring and perfuming materials, preservatives and antioxidants may be present in the formulated agents.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amounts of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and, intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound thereof as an active ingredient. Compounds of the present invention may also be administered as a bolus, electuary, or paste.

In solid dosage forms for oral administration (capsules, tablets, pills, dragees, powders, granules and the like), the coordination complex thereof is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating materials, such as agar-agar, calcium carbonate, potato or tapioca starch, alginic acid, certain silicates, and sodium carbonate; (5) solution retarding materials, such as paraffin; (6) absorption accelerators, such as quaternary ammonium compounds; (7) wetting materials, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring materials. In the case of capsules, tablets and pills, the compositions may also comprise buffering materials. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing materials. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds, may contain suspending materials as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a coordination complex of the present invention with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the agent. Formulations which are suitable for vaginal administration also include pessaries, tampons, creams, gels, pastes, foams or spray formulations containing such carriers as are known in the art to be appropriate.

Dosage forms for transdermal administration of a supplement or component includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the agent.

Ordinarily, an aqueous aerosol is made by formulating an aqueous solution or suspension of the agent together with conventional pharmaceutically acceptable carriers and stabilizers. The carriers and stabilizers vary with the requirements of the particular agent, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any of the compositions of the present invention or a combination thereof, and a means for facilitating compliance with methods of this invention. Such kits provide a convenient and effective means for assuring that the subject to be treated takes the appropriate agent in the correct dosage in the correct manner. The compliance means of such kits includes any means which facilitates administering the agent according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention will now be described in particularity with the following illustrative examples; however, the scope of the present invention is not intended to be, and shall not be, limited to the exemplified embodiments below.

Exemplification

Synthetic Method Overview

The compositions of the present invention include a carrier, a metal ion, and a second metal binding domain linked to an agent. In some embodiments, the carrier includes a hydrophobic group linked to a first metal binding domain. In other embodiments, the carrier includes a hydrophobic group, and hydrophilic group with a first end and a second end, and a first metal binding domain wherein the first end of the hydrophilic group is linked to the first metal binding domain and the second end of the hydrophilic domain is linked to the hydrophobic group. The first metal binding domain (FMBD) is capable of chelating the metal ion. A second metal binding domain (SMBD) linked to the agent is also capable of chelating the agent. The metal ion is capable of forming reversible linkages with the agent.

In one embodiment, a method of making a composition generally involves multi-step synthetic stages: 1) covalent modification of a hydrophobic group with two amino ends with a limited amount of metal binding domain such as DTPA anhydride; 2) modification of the product from step 1) with hydrophilic groups, such as, for example, carboxyl-activated methoxy PEG carboxyl; and 3) co-lyophilization of the product from step 2) with an agent in the presence of tent butanol and water followed by reconstitution in water, such as, for example, co-lyophilization with GLP to achieve formation of a supermolecular carrier-GLP complex.

EXAMPLES

Example 1

Preparation of a Hydrophobic Group with Two Amino Termini Using 1,18-octadecanedioic acid Alkyl chains with amino termini at both ends are normally available commercially. Alkyl chains with two carboxyl ends can be made into alkyl chains with two amino ends as follows: A mixture of one gin of 1,18-octadecanedioic acid (Mw=314.46; has 6.36 mmol carboxyl group) 0.92 g NHS [Mw=115.1; Hydroxysuccinimide; 25% molar excess] is added, 1.5 g EDC [Mw=191.7; N-(3-dimethylaminopropyl)-N'-ethylcarbodiimide hydrochloride; 25% molar excess] in 20 ml of dichloromethane, is slowly added to 9.5 ml ethylene diamine (Mw=60; 25 fold molar excess) in 20 ml of dichloromethane and the solution is stirred for 2 h. The reaction mixture is washed with aqueous 5% HCl, followed by brine drying over magnesium sulfate and concentration by rotary evaporation yielding the di-aminoterminated product [i.e., $(H_2N(CH_2)_2NHCO(CH_2)_{16}CONH(CH_2)_2NH_2]$.

Example 2

Preparation of N-hydroxysuccinamide Esters of Fatty Acids and Aromatic-alkyl Carboxylic Acids The N-hydroxysuccinamide esters of fatty and aromatic-alkyl carboxylic acids will facilitate the synthesis of hydrophobic chains or groups with metal binding domains and hydrophobic groups with hydrophilic groups of the present invention. These esters react readily with amino groups in aminated metal binding domains or aminated hydrophilic groups. The following method is adopted from Lapidot et al. [Lapidot, Y., Rappoport, S. and Wolman, Y. (1967) J. Lipid Res., 8, 142]: (i) prepare a 230 mM solution of N-hydroxysuccinimide by dissolving 3.45 g (30 nmol) in 30 ml of ethyl acetate dried over molecular sieve pellets in a stoppered 250-ml glass conical flask; (ii) to the above solution add 30 nmol of desired fatty acid; (iii) prepare a solution containing 30 mmol (6.18 g of dicyclohexyl carbodiimide in 10 ml ethyl acetate, and add it to the solution of fatty acid; (iv) allow the reaction to proceed overnight at room temperature; (v) remove the precipitated dicyclohexyl urea by filtration using a suction tap; (vi) evaporate the filtrate to dryness on a rotary evaporator, and purify it by re-crystallization from ethanol; and (vii) check the purity by TLC, using the solvent system: (a) chloroform, (b) petroleum (b.p. 40-60° C.)-diethyl ether, 8:2. Stain for N-hydroxysuccinimide and ester (red color) by spraying with 10% hydroxylamine in 0.1 M NaOH, followed after 2 min by 5% FeCb in 1.2 M HCl. Yields of 80-90% can be obtained.

Other activated fatty acids and aromatic alkyl carboxylic acids are commercially available (for example from Sigma-Aldrich Chem. Co., St Louis, Mo.) in the form of fatty acid anhydride, fatty acyl-halide, aromatic-alkyl-carboxyl-anhydride, or aromatic-alkyl-acyl-halide (such a -acyl-Cl and -acyl-Br).

Example 3

Preparation of methoxypoly(ethyleneglycol) Chain with Amino End[MPEG-amino]

Hydrophilic groups such as methoxy poly(ethyleneglycol) chains with amino termini at both ends are normally available commercially. However, if supplies are limited, methoxy poly(ethyleneglycol) chains with carboxyl (MPEG-carboxy) can be made into methoxy poly(ethyleneglycol) chains with ammo ends as follows: Ten gm of MPEG-carboxy (Mw=5 kDa; has 2 mmol carboxyl group) is dissolved in 50 ml dioxane To this solution, 0.29 g NHS [Mw=115.1; N-Hydroxysuccinimide; 25% molar excess] is added followed by addition of 0.48 g DCC [Mw=206; Dicyclohexylcarbodimide; ~50% molar excess] while stirring. After 2 h minutes, the mixture is cooled on ice, filtered through glass fiber paper, and added, drop-vise to an excess of diamine in dioxane and stirred overnight. Dioxane is removed under reduced pressure and the resultant MPEG-amine is purified by resolubilization in dichoromethane, filtration and ultrafiltration.

Example 4

Preparation of Hydrophobic Group with: Metal Binding Domain, a Metal Ion, and Agent [L-SMBD-Me-FMBD-H]

To make hydrophobic group with attached NTA, 0.5 gm (1.7 mmol) of stearoyl-Cl ((Mw=302.9) is dissolved in 50 ml of dichloromethane. To this solution, one gram (3.8 mmol) of NTA-lysine (Noc,Na-Bis(carboxymethyl)-L-Lysine Hydrate; Mw=263.26) is added and the reaction is allowed to proceed overnight with continuous stirring. The solution is dried the next day using a rotary evaporator, dissolved in 200 ml water to form a supermolecular structure with the NTA portion in the outside and the excess NTA-lysine is not incorporated in the supermolecular structure. This micelle solution is washed to remove using ultrafiltration membrane (UFP-50-E-3MA; Amersham Biosciences, Wesborough, Mass.) with 3 liters of water. The clean product which is hydrophobic NTA [H-FMBD] is lyophilized. Ten umol of metal binding agent with molar equivalent of Zn-Acetate in 0.5 nil water is added to 5.3 mg (~10 umol) of [H-FMBD] and is vortexed to form micelles. To this solution, 9.5 ml of vegetable oil is added resulting in a reversal of the micelle. This formulation can be enclosed into a soft-gel capsule for oral administration of the agent.

Example 5

Preparation of Hydrophobic Group with Protective Hydrophilic Chain [H-P]

Stearoyl-Cl will react spontaneously with amino groups of the protective hydrophilic chain to form amide bonds attaching the $CH_3(CH_2)_{16}CO-$ of the stearoyl-Cl to MPEG-amino. Briefly, 0.5 gm (1.7 mmol) of stearoyl-Cl ((Mw=302.9) is added to 50 ml of dichloromethane containing 5 g (1.0 mmol) of MPEG-amino, and the solution is stirred overnight. The solution is dried the next day using a rotary evaporator, dissolved in 200 ml of 70% ethanol, washed using an ultrafiltration membrane (UFP-5-E-3MA; GE Healthcare) with 2 liter of 70% ethanol, exchanged solvent to water by washing with 1 liter of water. The clean product which is hydrophobic group with protective hydrophilic chain is lyophilized.

The [L-SMBD-Me-FMBD-H] in example 5 is combined with [H-P]. Briefly, 10 umol of metal binding agent with molar equivalent of Zn-Acetate [L-SMBD-Me] in 5 ml of 50% water/tert butanol is added to 5.3 mg (~10 umol) of [FMBD-H]. The mixture is vortexed to form [L-SMBD-Me-FMBD-H]. To this solution, 10 umol of [H—P] in 5 ml of 50% water/tert butanol is added and vortexed. The solution is lyophilized and reconstituted in 5 ml PBS prior to administration into animals.

Example 6

Preparation of DTP A Terminated Alkyl Hydrophobic Group with Hydrophilic Group at the Other Terminal and Loading with Metal Binding Agent Through Zn Metal Bridge [L-SMBD-Me-FMBD-H-P]

Alkyl chains with amino terminal at both ends are normally available commercially. However, if supplies are limited, alkyl chains with two carboxyl ends can be made into alkyl chains with two amino ends as described above. Two hundred mg of alkyl chains with amino terminal at both ends (0.5 mmol; $[H_2N(CH_2)_2NHCO(CH_2)_{16}CONH(CH_2)_2NH_2]$; Mw=398) is dissolved in 20 ml of dichloromethane, 180 mg DTPA anhydride (0.55 mmol; Mw=357.3) is added, and the solution is stirred overnight. The next day, 2.5 grams of NHS activated carboxyl terminated methoxy polyethyleneglycol) [MPEGS; Mw=5 kDa; available from SunBio, Orinda, Calif.] is added, and the solution is stirred overnight. The solution is dried using a rotary evaporator, dissolved in 200 ml of 70% ethanol, washed using a ultrafiltration membrane (UFP-5-E-3MA; Amersham Biosciences, Wesborough, Mass.) with 2 liters of 70% ethanol, exchanged solvent to water by washing with 1 liter of water, and lyophilized. Before use, the material is dissolved in 50% tert-butanol/water, Zn-Acetate equivalent to the molar amount of DTPA is added followed by molar equivalent amount of metal binding diagnostic agent or metal binding therapeutic agent of choice. Once components are mixed, the mixture is lyophilized. These lyophilized components are reconstituted in water or PBS and spontaneously form supermolecular structures that release the associated metal binding diagnostic agent or metal binding therapeutic agent in a sustained manner once injected into the patient.

Example 7

Preparation of NTA Terminated Alkyl Hydrophobic Group with Hydrophilic Group Attached to Targeting Molecule at the Other Terminal and Loading with Metal Binding Agent Through Zn Metal Bridge [L-SMBD-Me-FMBD-H-P-T]

One gram of Wang resin [4-alkoxybenzyl alcohol resin (200-400 mesh); 0.9-1.2 mmol substitution/g; Bachem, Torrance, Calif.] is placed in a 50 ml peptide synthesis vessel with sintered glass frit with stopcock and PTFE plug (Kontes, Vineland, N.J.). With the stopcock closed, 1 gm of 1,18-octadecanedioic acid (Mw=314.46; has 6.36 mmol carboxyl group) dissolved in 10 ml of dichloromethane and 0.5 ml pyridine (~6.3 mmol; as catalyst) is added. The amount of 1,18-octadecanedioic acid is in excess to ensure that only one end of 1,18-octadecanedioic acid is linked to the resin. To this solution, 1.3 ml (~6.3 mmol) of DCC(NNdicyclohexylcabodiimide; Mw=206; heated to 35° C. to melt) is added and the vessel is capped and the 1,18-octadecanedioic acid is allowed to react with the resin overnight by placing the vessel in a shaker. The next day, the liquid is drained by removing the cap and opening the stopcock. The derivatized resin is rinsed with 40 ml of dichloromethane. Ten ml of dichloromethane and 2 ml ethylene diamine (Mw=60; 33 fold molar excess) is added after closing the stopcock, and 276 mg of NHS [Mw=115.1; Hydroxysuccinimide; 2 fold molar excess] is dissolved in the mixture. Five hundred ul(microliters) of DCC (~2.4 mmol; two fold molar excess) is added and the reaction is allowed to proceed for 2 hrs. This introduces primary amino group to the exposed carboxyl end of the resin anchored 1,18-octadecanedioic acid. After 2 hrs, the solution is drained off the resin and the resin is rinsed with 40 ml dichloromethane. Twelve grams (2.4 mmol; 2 fold molar excess) of dicarboxyl polyethylene glycol (Mw=5 kDa; with carboxyl group at both ends) is activated in 20 ml dichloromethane by adding 276 mg of NHS [Mw=115.1; Hydroxysuccinimide; 2 fold molar excess] and 500 ul (microliters) of DCC (~2.4 mmol; two fold molar excess). After 20 minutes, the solution is transferred to the vessel containing the resin with aminated 1,18-octadecanedioic acid and the reaction is allowed to proceed for 2 hrs. After 2 hrs, the solution is drained off the resin and the resin is rinsed with 40 ml dichloromethane. The terminal carboxyl of PEG attached to the resin is again completely activated, this time in aqueous solution. Briefly, 5 ml of 10 mM MES [2-(N-morpholino)ethanesulfonic acid] buffer, pH 4.7 with 0.172 g NHS [Mw=115.1; N-Hydroxysuccinimide; 25% molar excess] is added to the resin, followed by addition of 0.35 g EDC [Mw=191.7; N-(3-Dimethylaminopropyl)-N'-ethylcarbodiimide hidrochloride; 50% molar excess] and mixed in the shaker. After 20 minutes, the solution is drained quickly and 10 ml of 200 mM HEPES buffer, pH 7.4 containing 5 mmol RGD-amide (Arginine-Glycine-Aspartate-amide; an example of targeting molecule the specifically localizes to cancer vasculature), and the solution is mixed in the shaker overnight. The next day, the solution is drained and the resin is rinsed with 40 ml of dichloromethane. The [-H-P-T] is released from the resin by adding 10 ml of 50% TFA in DCM and incubating for 2 hrs at 25° C. The solution containing liberated [-H-P-T] is drained off the resin and TFA and dichloromethane are rotary evaporated out. The [-H-P-T] is then activated at the carboxyl end by adding 5 ml of 10 mM MES [2-(N-morpholino)ethanesulfonic acid] buffer, pH 4.7 with 0.172 g NHS [Mw=115.1; N-Hydroxysuccinimide; 25% molar excess] is added to the resin, followed by addition of 0.29 g EDC [Mw=191.7; N-(3-Dimethylaminopropyl)-N'-ethylcarbodiimide hidrochloride; 25% molar excess] and mixed in the shaker for 20 minutes. After 20 minutes, 10 ml of 200 mM HEPES buffer, pH 7.4 containing 5 mmol of NTA-lysine (Nα,Nα-Bis(carboxymethyl)-L-Lysine Hydrate; Mw=263.26) is added and the reaction is allowed to proceed overnight with continuous stirring. The solution is dried using rotary evaporator, dissolved in 200 ml of 70% ethanol, washed using ultrafiltration membrane (UFP-5-E-3MA; Amersham Biosciences, Wesborough, Mass.) with 2 liters of 70% ethanol, exchanged solvent to water by washing with 1 liter of water, and lyophilized. Before use, the material is dissolved in 50% tert-butanol/water, Zn-Acetate equivalent to the molar amount of NTA is added followed by the molar equivalent amount of a metal binding therapeutic agent of choice. Once the components are mixed, the mixture is lyophilized. These lyophilized components are reconstituted in water or PBS and spontaneously form supermolecular structures that localize to cancer tissues and release the associated metal binding therapeutic agent in a sustained manner once injected to the cancer patient.

Although the above examples have been described with the targeting group attached at the end of solid-phase synthesis. A method where the peptide targeting group is synthesized on the resin using standard peptide synthesis know to those with skill in the art, either on benzylhydramine resin or similar resin (Bachem, Torrance, Calif.) that may or may not result in amidated product. Once the targeting group is synthesized, a hydrophilic group may be added to the free amino group of the targeting group. This may be followed by the attachment of the hydrophobic group and the first metal binding domain. The whole component may then be de-protected and released from the resin. The attachment of agent through the metal bridge is as described above.

Although the foregoing invention has been described in some detail by way of illustration and example for the purposes of clarity of understanding, one skilled in the art will easily ascertain that certain changes and modifications may be practiced without departing from the spirit and scope of the appended claims. The supermolecular structures illustrated in the Figures are only several of many supermolecular structures possible and may change depending on the solvent or excipient in which the compositions are suspended.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A composition with a metal bridge comprising:
  a first molecule comprising:
    a first hydrophobic group comprising a first and second end;
    a first metal binding domain (FMBD) covalently linked to the first end of the first hydrophobic group;
    a metal ion chelated to the FMBD;
    an active agent comprising a second metal binding domain (SMBD) coordinately bonded to the metal ion; and
    a hydrophilic group,
  wherein the hydrophilic group is covalently linked to the second end of the first hydrophobic group.

2. The composition of claim 1, further comprising a second molecule comprising:
  a second hydrophobic group; and
  a second hydrophilic group, wherein the hydrophilic group is covalently linked to the second hydrophobic group.

3. The composition of claim 2, further comprising a third molecule comprising:
  a third hydrophobic group; and
  a third hydrophilic group comprising a first and second end, wherein the first end of the third hydrophilic group is covalently linked to the third hydrophobic group and
  a targeting group covalently linked to the second end of the third hydrophilic group.

4. The composition of claim 1, further comprising a second molecule comprising:
  A second hydrophobic group; and
  a second hydrophilic group comprising a first and second end, wherein the first end of the second hydrophilic group is covalently linked to the second hydrophobic group; and
  a targeting group covalently linked to the second end of the second hydrophilic group.

5. The composition of claim 1, further comprising:
  a targeting group covalently linked to the hydrophilic group.

6. The composition of claim 5, further comprising a second molecule comprising:
- a second hydrophobic group; and
- a second hydrophilic group comprising, wherein the second hydrophilic group is covalently linked to the second hydrophobic group.

7. The composition of claim 6, further comprising:
a third metal binding domain (TMBD) covalently linked to the second hydrophobic group.

8. The composition of any one of claims 1-7, wherein the FMBD, the SMBD, or the TMBD is selected from a nitrogen containing poly carboxylic acid or a polypeptide.

9. The composition of any one of claims 1-7, wherein the metal ion is a transition metal ion (d-block of the periodic table).

10. The composition of any one of claims 1-7, wherein the active agent is an imaging agent or a therapeutic agent.

11. The composition of any one of claims 3-7, wherein the targeting group is selected from the group consisting of an antibody, a cell surface receptor ligand, a cell surface receptor binding drug, a cell surface binding saccharide ligand, an extracellular matrix ligand, a cytosolic receptor ligand, a growth factor, a cytokine, an incretin, a hormone, and a lectin.

12. The composition of any one of claims 1-7, wherein the FMBD, the SMBD, or the TMBD are individually selected from N-(hydroxy-ethyl)ethylenediaminetriacetic acid; nitrilotriacetic acid (NTA); ethylene-bis(oxyethylene-nitrilo) tetraacetic acid; 1,4,7,10-tetraazacyclodo-decane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); or 1,2-diaminocyclohexane-N,N,N',N'-tetraacetic acid.

13. The composition of claim 8, wherein the FMBD, the SMBD, or the TMBD is a metal binding polypeptide of formula: (AxHy)p where A is any amino acid, H is histidine, x is an integer from 0-6; y is an integer from 1-6; and p is an integer from 1-6.

14. The composition of any one of claims 1-7, wherein the hydrophobic group has a molecular weight ranging from about 50 to about 1000 Daltons.

15. The composition of any one of claims 1-7, wherein the hydrophobic group comprises one or more linear fatty acyl groups with a formula of $[CH_3(CH_2)_xCO-]$ wherein x is an integer from 6-50.

16. The composition of any one of claims 1-7, wherein the hydrophobic group is a branched or straight chain $C_5$-$C_{50}$ alkyl, a substituted branched or straight chain $C_5$-$C_{50}$ alkyl, poly-glycine, a substituted poly-glycine, poly-alanine, poly-valine, poly-leucine, poly-isoleucine, poly-phenylalanine, poly-proline, poly-methionine, phenyl, napthyl, cholesterol, vitamin D, or vitamin E.

17. The composition of any one of claims 1-7, wherein a hydrophobic group has a general formula of $[P_vN_wC_xH_yO_z-]$ wherein v is an integer from 0-3; w is an integer from 0-3; x is an integer from 8-48; y is an integer from 15-95; and z is an integer from 1-13.

18. The composition of any one of claims 1-7, wherein a hydrophilic group comprises a polymer selected from poly (ethylene glycol); alkoxy poly(ethyleneglycol); methoxy poly(ethylene glycol); dicarboxylic acid esterified poly(ethylene glycol) monoester; poly(ethylene glycol)-diacid; copolymer of poly(ethylene glycol); poly(ethylene glycol) monoamine; methoxy poly(ethyl ene glycol) monoamine; methoxy poly(ethyl ene glycol) hydrazide; methoxy poly (ethyl ene glycol) imidazolide; blockcopolymer of poly(ethylene glycol); poly-lactide-glycolide co-polymer; polysaccharide; oligosaccharides; polyamidoamine; and polyethyleneimine.

19. A method of delivering an active agent to a target site comprising administration of a composition to a subject, the composition comprising:
- a first molecule comprising:
    - a first hydrophobic group comprising a first and second end;
    - a first metal binding domain (FMBD) covalently linked to the first end of the first hydrophobic group;
    - a metal ion chelated to the FMBD;
    - an active agent comprising a second metal binding domain (SMBD) coordinately bonded to the metal ion;
    - a hydrophilic group, wherein the hydrophilic group is covalently linked to the second end of the first hydrophobic group
- wherein after administration of the composition to the subject, the active agent is released in a sustained manner, and the active agent is a therapeutic or a diagnostic agent.

* * * * *